(12) United States Patent
Jensen et al.

(10) Patent No.: US 10,912,757 B2
(45) Date of Patent: Feb. 9, 2021

(54) PRODUCT COMPRISING RED CLOVER EXTRACT AND METHODS FOR PRODUCING THE SAME

(71) Applicant: HERRENS MARK APS, Norre Aaby (DK)

(72) Inventors: Michael Mohr Jensen, Norre Aaby (DK); Per Bendix Jeppesen, Ega (DK); Max Norman Tandrup Lambert, Aarhus (DK); Anne Cathrine Sonderstgaard Thorup, Hinnerup (DK)

(73) Assignee: HERRENS MARK APS, Norre Aaby (DK)

( * ) Notice: Subject to any disclaimer, the term of this patent is extended or adjusted under 35 U.S.C. 154(b) by 232 days.

(21) Appl. No.: 16/036,794

(22) Filed: Jul. 16, 2018

(65) Prior Publication Data

US 2018/0333387 A1    Nov. 22, 2018

Related U.S. Application Data

(62) Division of application No. 14/651,742, filed as application No. PCT/DK2013/050428 on Dec. 12, 2013, now abandoned.

(30) Foreign Application Priority Data

Dec. 12, 2012  (DK) ................................ 2012 70780

(51) Int. Cl.

| A61K 31/352 | (2006.01) |
|---|---|
| A61K 35/744 | (2015.01) |
| A61K 36/288 | (2006.01) |
| A61K 36/48 | (2006.01) |
| A61K 47/46 | (2006.01) |
| C12P 17/06 | (2006.01) |

(52) U.S. Cl.
CPC .......... *A61K 31/352* (2013.01); *A61K 35/744* (2013.01); *A61K 36/288* (2013.01); *A61K 36/48* (2013.01); *A61K 47/46* (2013.01); *C12P 17/06* (2013.01)

(58) Field of Classification Search
None
See application file for complete search history.

(56) References Cited

U.S. PATENT DOCUMENTS

| 6,132,778 A | 10/2000 | Kasler |
|---|---|---|
| 7,396,855 B2 | 7/2008 | Setchell |
| 2004/0228931 A1 | 11/2004 | Chokshi |

FOREIGN PATENT DOCUMENTS

| CN | 1475227 | | 2/2004 |
|---|---|---|---|
| CN | 1981799 A | | 6/2007 |
| CN | 101558899 A | * | 10/2009 |
| EP | 1174144 A1 | | 1/2002 |
| EP | 1391208 A1 | | 2/2004 |
| EP | 1637609 A1 | | 3/2006 |
| JP | 2010227125 A | * | 10/2010 |
| KR | 10-2003-0071396 A | | 9/2003 |
| WO | 1999038509 A1 | | 8/1999 |
| WO | 2010066852 | | 6/2010 |
| WO | 2012007978 A2 | | 1/2012 |

OTHER PUBLICATIONS

Shurkhno (Applied Biochemistry and Microbiology (2006), vol. 42, No. 2, pp. 204-209).*
Chinese Traditional and Herbal Drugs, Table 1, pp. 309-312 (Feb. 2, 2006).
Beck et al, "Phytoestrogens Derived from Red Clover: An Alternative to Estrogen Replacement Therapy?". J. Steroid Biochem. and Mol. Biol., 94:499-518 (Apr. 2005).
Xu et al, "Recovery of Isoflavoids from Red Clover Flowers by a Membrane-Based Process," Innovative Food Sciences and Emerging Technologies, 7:251-256 (Sep. 2006).

* cited by examiner

*Primary Examiner* — Susan Hoffman
(74) *Attorney, Agent, or Firm* — BakerHostetler

(57) ABSTRACT

The invention relates to a composition comprising isoflavones from red clover. The red clover extract has been fermented to obtain a composition comprising aglycone isoflavones. The fermentation is preferably performed by a lactic acid bacteria or fermented dandelion extract.

25 Claims, 7 Drawing Sheets

PRODUCT COMPRISING RED CLOVER EXTRACT AND METHODS FOR PRODUCING THE SAME

Figure 1:
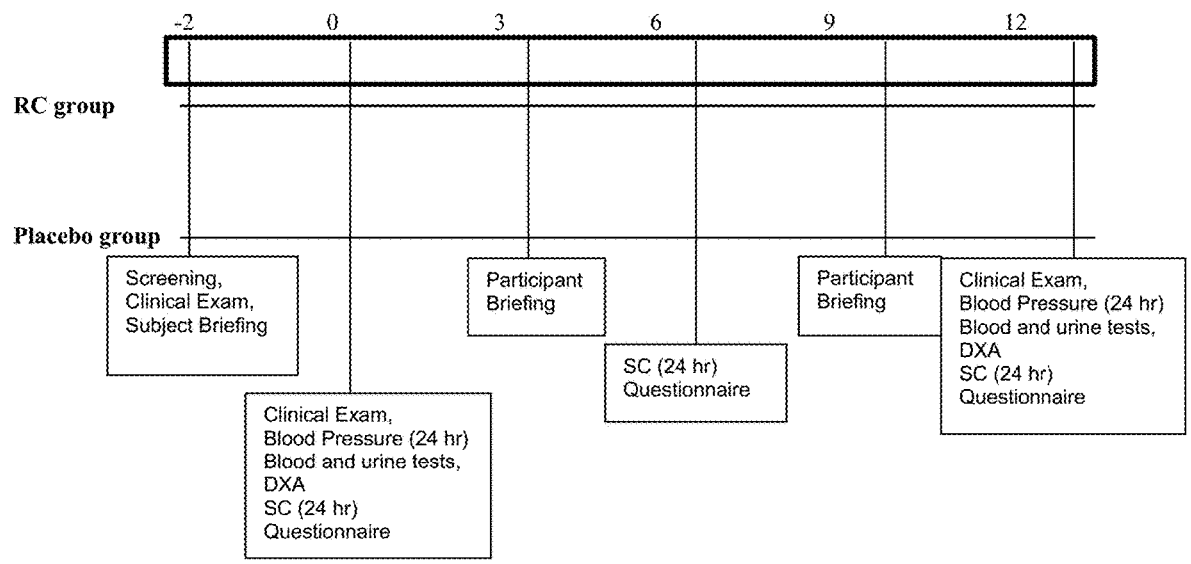

This application is a divisional application of U.S. patent application Ser. No. 14/651,742, filed Jun. 12, 2015, now abandoned, which is a 371 Application of International Patent Application No. PCT/DK2013/050428, filed Dec. 12, 2013 which claims priority to DK Application No. PA 2012 70780, filed Dec. 12, 2012, the disclosure of each of which are incorporated by reference herein in their entireties of any and all purposes.

FIELD OF INVENTION

The invention relates to a composition comprising red clover extract. The red clover extract has been fermented to obtain a composition comprising the aglycone form of isoflavones. The fermentation is preferably performed by a lactic acid bacteria.

BACKGROUND

The human menopause is associated with increased risk of osteoporosis, negative changes in lipid status, cardiovascular events, vasomotor symptoms and reduced quality of life. The aetiology of these effects is thought to derive from the deficiency and/or dysregulation of normal estrogen homeostasis caused by the menopause. Hormone replacement therapy with estrogen has proven to be effective in treating osteoporosis and vasomotor symptoms associated with the menopause. Hormone replacement therapy has however proved to be of limited use in this regard due to the inherent problems regarding the side effects of treatment, i.e. increased risks for cancer (breast, endometrial and ovarian), cardiovascular disease (CVD), liver disease and thromboembolic disorders. As such, there is both scientific and commercial value in developing an alternative therapy for the treatment of age related osteopenia and menopause symptoms that is free from the negative side effects associated with hormone replacement therapy.

Plant derived compounds that emulate the structure and behaviour of estrogen (known as phytoestrogens or isoflavones) have been of significant interest lately, as they may occupy the roles of estrogen without incurring negative effects associated with hormone replacement therapy. Red Clover is one plant species that is known to be rich in isoflavones. Hence, extracts from this plant may potentially proffer preventative or therapeutic properties against menopause related risk factors.

Soy and red clover (*Trifolium pratense*) isoflavones have been used for some time instead of estrogens in the treatment of post-menopausal syndrome since they show antioxidizing, antitumor, antiinflammatory and cardioprotective activity.

Soy has a low content of formononelin, ononin and Biochanin A which is present in red clover in high amounts. Soy has, in contrast to red clover, a high content of daidzein and genistein [Nordentoft et al., J Agric Food Chem. 2008 June 25; 56(12):4377-85].

Isoflavones are shown to act as selective estrogen receptor modulators (SERMs) meaning the compounds retain the capacity to bind to estrogen receptors (ERs) but exhibit behaviour distinct from that of estrogen. In contrast to estrogen, isoflavones bind to estrogen receptor-β (ERβ) with high affinity and to a lesser degree act as weak ERα ligands. ERs are expressed in high concentrations in non-gonadal tissues, such as adipose, brain, kidney, intestinal mucosa, endothelial cells, liver, lung parenchymal cells, bone tissues and bone marrow. These tissues require certain stimulation by estrogen in order to function normally. Hence, selective stimulation of these through the binding behaviour of isoflavones may allow these compounds to adopt the regulatory roles of estrogen (in tissues with high ERβ expression) without over-stimulating tissues with high ERα expression, thereby not inducing cancer risk. This is of importance to women in the menopause who are suffering from natural estrogen deficiency and/or dysregulation; as deficiency in estrogen is known to disrupt bone tissue regulation, which then further leads to accelerations in bone mineral resorption rates and extends resorption phases of bone remodelling. These effects have been noted both in humans and in ovariectomised (menopause induced) rats.

Red Clover (RC) offers an economically viable source of isoflavones for use in medical, functional food and therapeutic applications, as it is broadly utilised as a fodder crop for the enhancement of soil quality. Among its various capabilities are most important its capacity fix nitrogen, act as a conditioner and attract beneficial insects.

A number isoflavones are present in RC, namely daidzein, genistein, formononetin and biochanin A. All are known to have ER binding capability; it is the abundance of formononetin and biochanin A that differentiate RC's profile from soy [Beck V, Rohr U, Jungbauer a: Phytoestrogens derived from red clover: an alternative to estrogen replacement therapy? *The Journal of steroid biochemistry and molecular biology* 2005, 94:499-518]. Animal trials testing RC derived isoflavones have shown they can attenuate BMD of ovariectomised rats and in vitro trials have demonstrated capabilities of isoflavones to mediate intercellular signalling between osteoblasts and osteoclasts through the up-regulation of osteoprotegerin synthesis. Human trials have shown promising effects of RC derived isoflavones on bone biomarkers for resorption and have achieved variable success on increasing markers of bone formation; nevertheless there remains a strong potential for isoflavones to blunt bone mineral resorption and potentially stimulate formation. Formononetin, in particular, may have the potential not only to attenuate the resorption of bone tissue but also to stimulate anabolism by promoting the differentiation of osteoblasts from mesencymal stem cell precursors.

The most abundant isoflavones are daizin and genistin, which are glucoconjugates of daidzein and genistein. Other isoflavones, present in particular in red clover extracts, comprise biochanin A, formonetin A and glycitein characterized in the presence of methoxy groups on the phenyl rings.

EP1637609 discloses an equol-enriched red clover extract obtainable through fermentation with *Eubacterium limosum* of isoflavones naturally contained in the extract. EP1637609 discloses that the extract can be used for treatment of the post-menopausal syndrome.

WO99/38509 discloses a method for removing a sugar portion from isoflavanoids derived from red clovers to produce an isoflavonoid aglycone. The method comprises addition of acid to the red clover extract.

There is a need for development of isoflavone preparations with improved properties and/or improved concentration and/or increased bioavailability, e.g. improved concentration and/or increased bioavailability of genistein, and/or derivatives thereof.

SUMMARY OF THE INVENTION

The present invention provides a composition having a fixed, high amount of a phytoestrogen compound such as e.g. naturally occurring isoflavones. More particularly the present invention provides a composition of red clover extractable ingredients having a fixed, high amount of a phytoestrogen compound such as e.g. naturally occurring isoflavones. The invention particularly relate to lactic acid fermentation of red clover extractable ingredients having a fixed, high amount of a phytoestrogen compound such as e.g. naturally occurring isoflavones.

More particularly, the present invention provides a combination comprising a high, fixed content of a plant hormone in the form of a phytoestrogen compound, preferably naturally occurring isoflavones fermented by one or more lactic acid bacteria.

The present invention represents a potential new breakthrough in treatment of e.g. postmenopausal symptoms including hot flashes, osteoporosis, cardiovascular diseases, metabolic syndrome, insulin resistance and type 2 diabetes.

FIGURE LEGENDS

FIG. 1: A schematic representation of the study design. The far left shows the 2 groups, those receiving RC extract and the placebo below. Screening and briefing took place 2 weeks prior (−2) to project start and included the measurement of baseline values (BMI, Age, self-reported HF frequency, FSH level, habitual and medical status). Post screening and randomisation administration of either placebo or RC extract took place at 0 (start). At week 0 and week 12, blood and urine samples were taken and analysed, blood pressure (BP) and DXA scans. Weeks 0, 6 and 12 particpants were requested to fill out a green menopause questionnaire and skin conductance (SC). Both 24 hour measurements of SC and BP were carried out on separate days.

Figure 2:
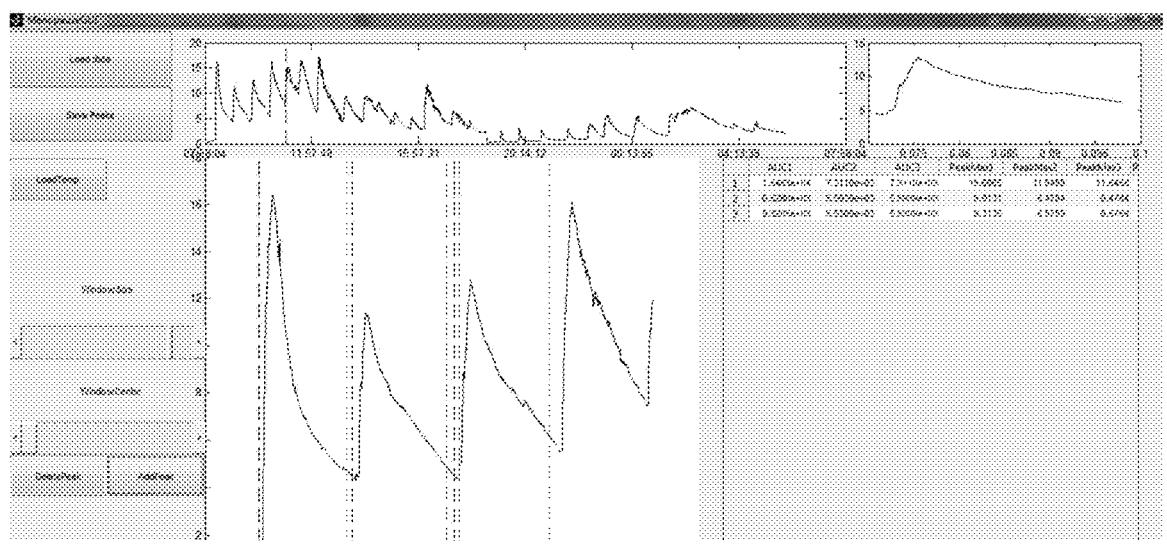

FIG. 2: MenopauseGUI interface developed for determination of HF frequency (i.e. the number of HFs in 22 hours) and HF intensity is defined as area under the curve (AUC).

Figure 3:
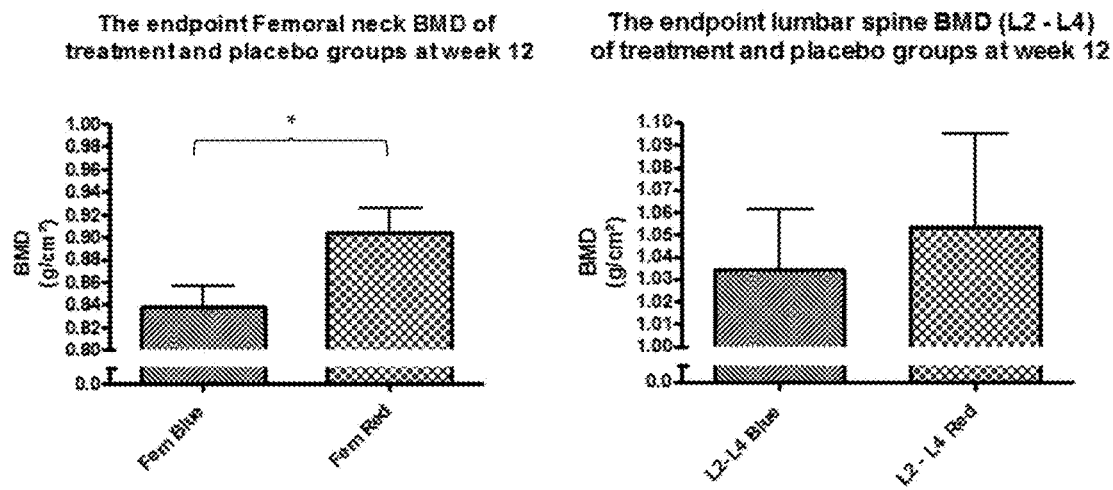

FIG. 3: The intergroup difference between final DXA measurements of bone mineral densities in red (treatment) and blue (placebo) groups. Graph A represents change in BMD at the femoral neck and graph B displays difference in BMD at the lumbar spine. Unpaired T testing showed a significant difference between the absolute values of data sets in graph A (P 0.0316). There was no significant difference found in graph B. T bars represent SEM. * indicates $p<0.05$.

Figure 4:
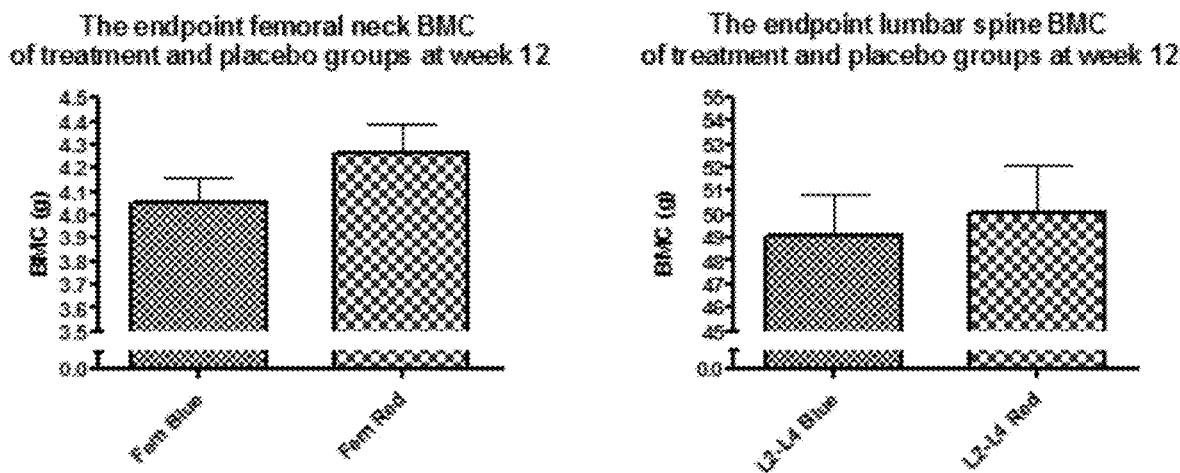

FIG. 4: The difference between the final DXA measurements of bone mineral content in red (treatment) and blue (placebo) groups. Graph A represents change in BMC at the femoral neck and graph B displays difference in BMC at the lumbar spine. T bars represent SEM. These data demonstrate the tendency that the Red Clover group increases BMC.

Figure 5:
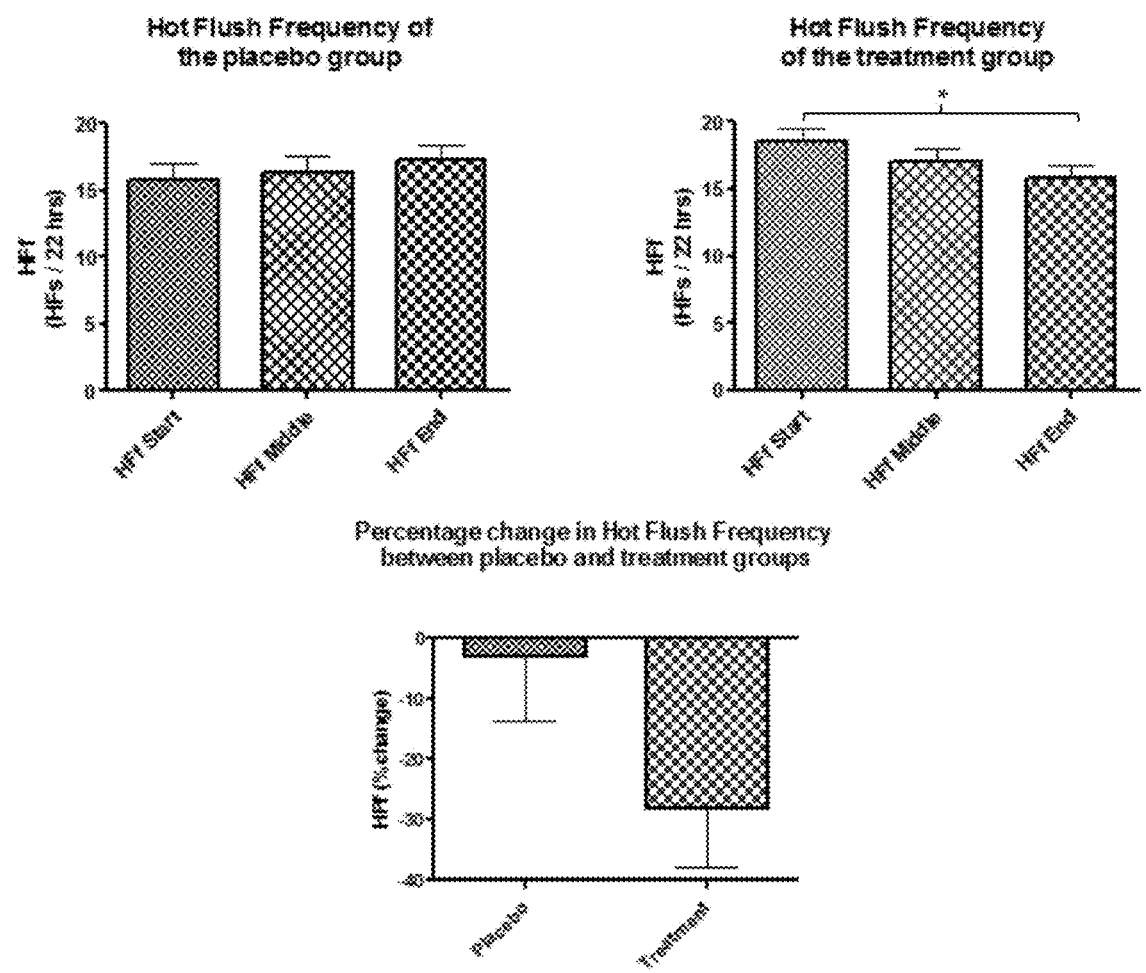

FIG. 5: The changes (from baseline) between the HF frequency values of treatment and placebo groups. AB represents differences in absolute values of HF frequency within placebo (A) and treatment (B) groups respectively, respectively. C displays percentile change (from week 0-12) in HF frequency between treatment and placebo. Paired student T tests reveal a significant difference between the absolute values from week 0 and 12 in the B data set (P 0.0168) and no significant change in the A grouping. Unpaired student T tests showed no significant differences between start and end results in A and B data sets. No significant difference was found between HF frequency (% change) between placebo and treatment groups in C data set. T bars represent SEM. * indicates $p<0.05$ FIG. 6: The relative change (from baseline to week 12) between the HF intensity values of treatment and placebo groups adjusting for increases in sweat secretion with a seasonal variation factor. This graph displays the difference in HF intensity within the placebo group compared to the equivalent changes within the treatment group, where the mean baseline values are normalised to 1. Paired student T testing showed a significant reduction between the start and end values of the treatment group (p 0.0396). No significant differences were found between the start and end values of the placebo group. * indicates $p<0.05$. T bars represent SEM.

Figure 7:
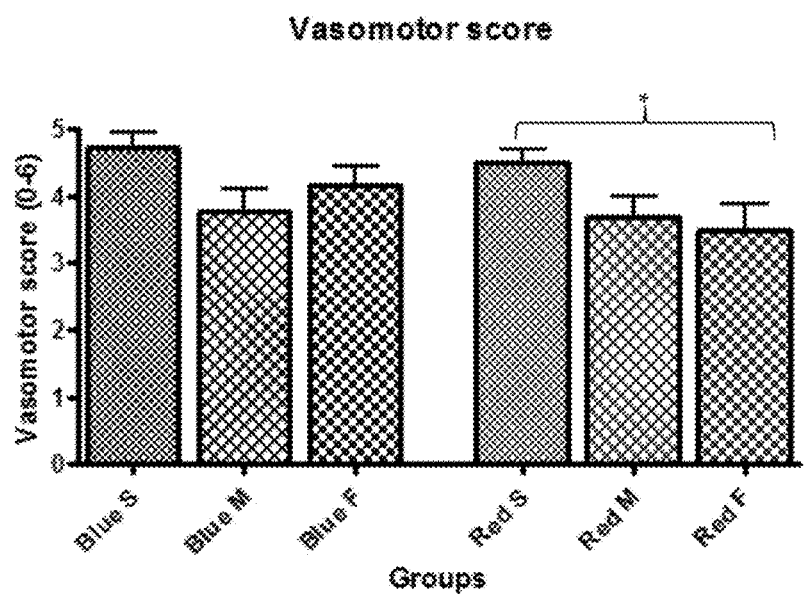

FIG. 7: A graph representing the cumulative vasomotor values from the Green Menopause index questionnaires completed by both the placebo (Blue) and treatment (Red) groups, at baseline, middle and end points of the trial. Paired T testing showed significant a decrease in vasomotor symptoms within the treatment group. Start, Middle and Finish are denoted by S, M and F respectively. * indicates $p<0.05$ FIG. 8: A graph representing the generally pro inflammatory cytokines analysed with bio-rad multiplex assay from both the placebo (Blue) and treatment (Red) groups. Paired T testing showed no significant difference in IL-5 (graph A), IL 12-p70 (graph B) or INF gamma (graph C) in either treatment or the placebo group from start (S) to end (E). T Bars denote SEM.

Figure 9:
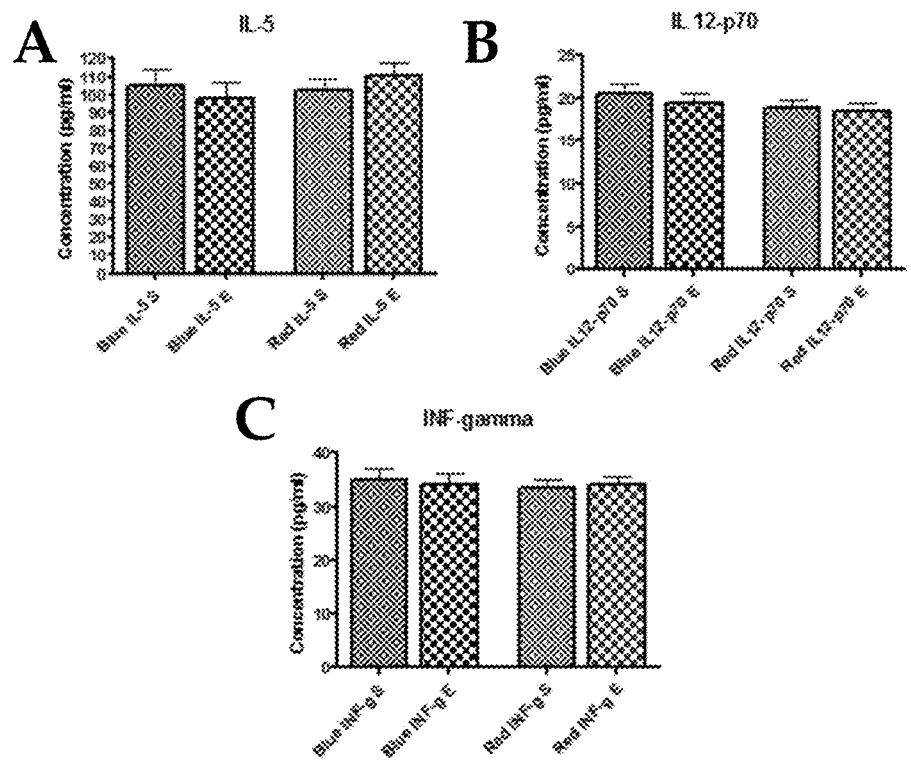

FIG. 9: A graph representing the generally pro inflammatory cytokines analysed with bio-rad multiplex assay from both the placebo (Blue) and treatment (Red) groups. Paired T testing showed no significant difference in IL-5 (graph A), IL 12-p70 (graph B) or INF gamma (graph C) in either treatment or the placebo group from start (S) to end (E). T Bars denote SEM.

Figure 10:
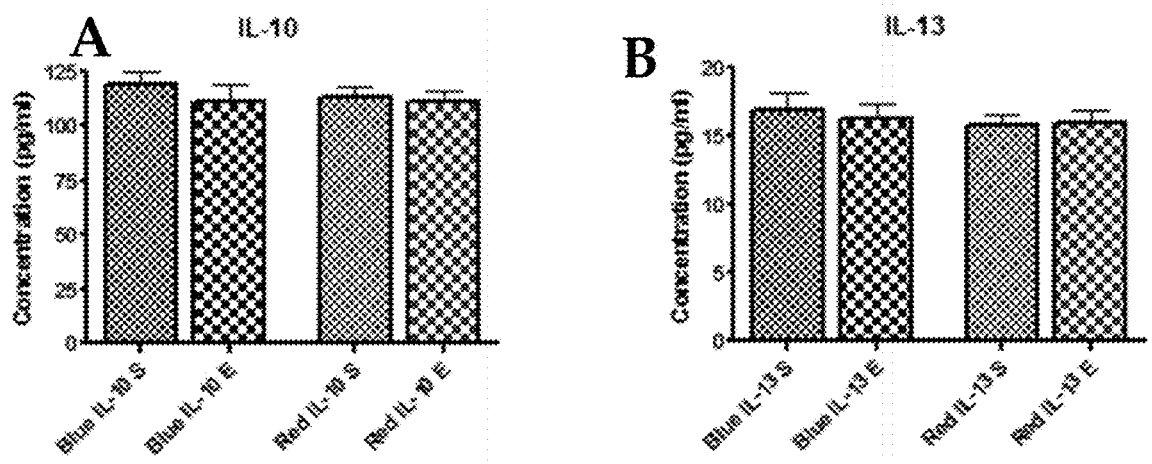

FIG. 10: A graph representing the generally anti-inflammatory cytokines analysed with bio-rad multiplex assay from both the placebo (Blue) and treatment (Red) groups. Paired T testing showed no significant difference in IL-10 (graph A) and IL-13 (graph B) in either treatment or the placebo group from start (S) to end (E). T Bars denote SEM.

Figure 11:
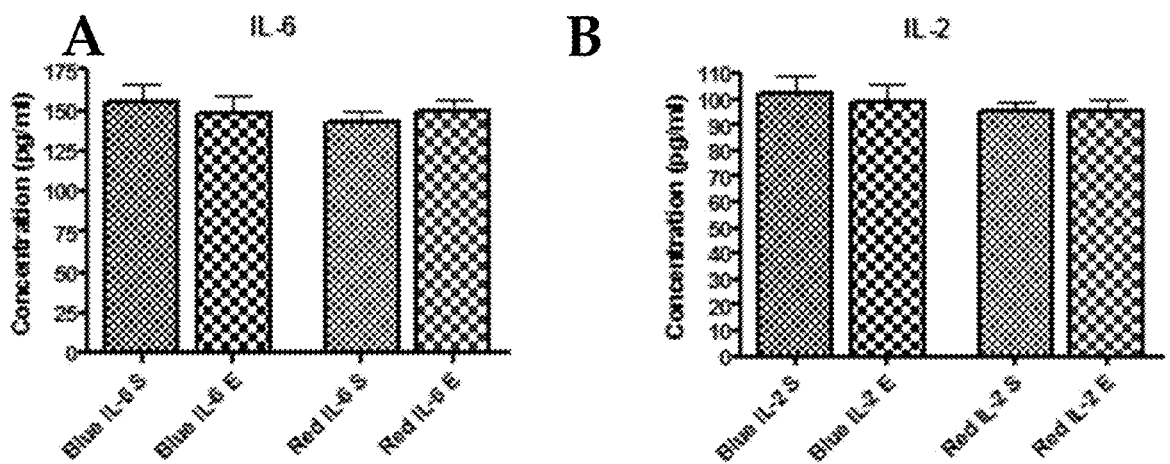

FIG. 11: A graph representing the biphasic immunomodulatory cytokines analysed with bio-rad multiplex assay from both the placebo (Blue) and treatment (Red) groups. Paired T testing showed no significant difference in IL-6 (graph A) or IL-2 (graph B) in either treatment or the placebo group from start (S) to end (E). T Bars denote SEM.

Figure 12:
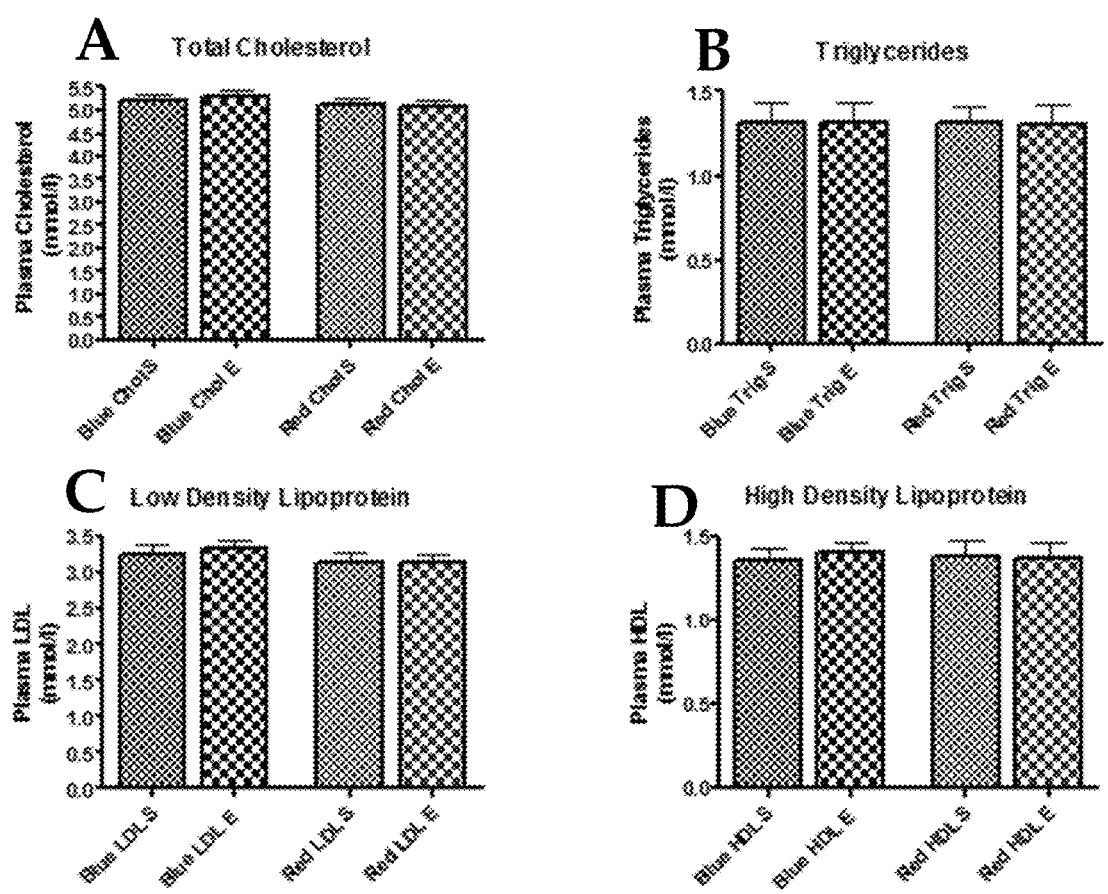

FIG. 12: An array of graphs representing total cholesterol (A), triglycerides (B), low density lipoprotein (C) and high density lipoprotein (D) of placebo (Blue) and treatment (Red) groups. Start and end point measurements are denoted by S and E respectively. Paired T tests failed to reveal any significant differences in total cholesterol, triglycerides, LDL or HDL plasma concentrations in either the treatment or the placebo group from start (S) to end (E). T Bars denote SEM.

ABBREVIATIONS

BMC: Bone Mineral Content
BMD: Bone Mineral Density
BMI: Body Mass Index
BP: Blood Pressure
CRP: C reactive protein
CVD: Cardiovascular Disease
DNA: Deoxyribonucleic acid
ER: Estrogen Receptor
ERE: Estrogen response element sequences
FSH: Follicle Stimulating Hormone
HF: Hot Flushes
HFi: Hot Flush intensity Hs-CRP: High sensitivity C-reactive protein
IL-12: Interleukin 12
IL-13: Interleukin 13
IL-2: Interleukin 2
IL-4: Interleukin 4
IL-5: Interleukin 5
IL-6: Interleukin 6
IL-10: Interleukin 10
INF-γ: Interferon gamma
PMS: Pre-Menstrual Syndrome
RC: Red Clover
SC: Skin Conductance
SEM: Standard Error of Means
SD: Standard Deviation
NS: Non-significant
NMR: Nuclear Magnetic Resonance
HPLC: High Performance Liquid Chromatography
rp-HPLC: Reverse Phase-High Performance Liquid Chromatography
LC: Liquid Chromatography
MS: Mass Spectrometry
UV: Ultraviolet
LDL: Low Density Lipoprotein
HDL: High Density Lipoprotein
TG: Triglycerides
HF: Hot Flushes Definitions Red clover: *Trifolium pratense* (red clover) is a species of clover, native to Europe, Western Asia and northwest Africa, but planted and naturalised in many other regions. It is an herbaceous, short-lived perennial plant, variable in size, growing to 20-80 cm tall. The leaves are alternate, trifoliate (with three leaflets), each leaflet 15-30 mm long and 8-15 mm broad, green with a characteristic pale crescent in the outer half of the leaf; the petiole is 1-4 cm long, with two basal stipules. The flowers are dark pink with a paler base, 12-15 mm long, produced in a dense inflorescence. Red clover comprises the following species: *Trifolium pratense pratense, Trifolium pratense americanum, Trifolium pratense frigidum, Trifolium pratense maritimum, Trifolium pratense parviflorum, Trifolium pratense sativum*, and *Trifolium pratense villosum*. Red clover also comprises the following species: *Rajah* (a Danish species), *Nordi* (a Norwegian species); *Jesper* (a Finish species), *Joioinen* (a Finish species), and *Pawera* (a species from New Zealand).

Red clover extract: A red clover extract is a composition comprising molecules derived from red clover. In one embodiment the extract is an aqueous extract comprising essentially no red clover biomass. Red clover (*Trifolium pratense*) extracts and methods for the preparation thereof are disclosed, for example, in EP1391208 and in EP1174144. Alternatively the red clover extract can be prepared as described in Example 1.

Phytoestrogen: The term phytoestrogens has in one embodiment the same meaning as isoflavones and these terms are used interchangely herein.

Phytoestrogen compounds: are naturally occurring plant substances, which are either structurally or functionally similar to 17β-estradiol or generate estrogenic effects. Phytoestrogens consist of a number of classes including isoflavones, coumestans, lignans and resorcylic acid lactones. Examples of isoflavones according to the present invention are genistein, daidzein, equol, glycitein, biochanin A, formononetin, and O-desmethylangolesin.

Aglycone form of isoflavons: Phenolic compounds from red clover known as isoflavones exist in glycoside or aglycone (without the glycoside part) forms. Fermentation increases isoflavone aglycone content in the red clover extract. While all isoflavones are absorbed into the mucosa of the small intestine, the aglycone form is absorbed at a greater rate and also has higher antioxidant activity than the glycoside form.

Lactic acid bacteria (LAB): Lactic acid bacteria is defined as any lactic acid bacteria capable of fermenting red clover isoflavones in a red clover extract to obtain a red clover extract wherein the majority of the isoflavones—such as more than 80%, 90%, 95% or 99%—is on the aglycone form.

Dandelion: *Taraxacum* (Dandelion) is a large genus of flowering plants in the family Asteraceae.

The term "naturally occurring" substance as used herein refers to a substance originally isolated from a natural source, such as an animal or a plant, for example a red clover plant, or modified forms of such a substance. The naturally occurring substance for use in a composition according to the present invention may be included in a composition according to the present invention as part of the natural source or in any type of extract, isolate or the like thereof, or it may have been isolated from a plant source or synthesized biologically, microbiologically, or chemically or by any other means.

Metabolic syndrome: Even though there is no internationally agreed definition for the metabolic syndrome, the term as used herein shall be understood to relate to the occurrence in a subject of at least two of the following: i) impaired glucose tolerance, ii) elevated blood pressure, iii) hypertriglyceridaemia and low HDL-cholesterol, iv) insulin resistance, and v) obesity. The occurrence of a condition characterised by one or more of impaired glucose tolerance, elevated blood pressure, hypertriglyceridaemia and low HDL-cholesterol, insulin resistance, and obesity will depend on variables such as sex, age, body weight, physical condition and the like, and general WHO guidelines will generally be adhered to when evaluating the occurrence of any one of the above-mentioned conditions.

Treatment: a treatment can be prophylactic, curative, and/or ameliorating of the medical indication. Treatment can result in amelioration of one or more symptoms of the medical indication or of all symptoms of the medical indication. Treatment can alternatively completely remove one or more or all symptoms of the medical indication.

The treatment can also be prophylactic—i.e. preventing or inhibiting development of the medical indication.

DETAILED DESCRIPTION OF THE INVENTION

Method of Making the Composition

Phenolic compounds from red clover known as isoflavones exist in glycoside or aglycone (without the glycoside part) forms. Fermentation increases isoflavone aglycone content in the red clover extract. While all isoflavones are absorbed into the mucosa of the small intestine, the aglycone form is absorbed at a greater rate and also has higher antioxidant activity than the glycoside form.

Red clover (*Trifolium pratense*) extracts and methods for the preparation thereof are disclosed, for example, in EP1391208 and in EP1174144. Alternatively the red clover extract can be prepared as described in Example 1.

In one preferred embodiment the red clover extract is organic. The present invention relates in one aspect to a method of making a fermented red clover extract comprising the steps of
i) providing a red clover extract
ii) providing one or more lactic acid bacteria species
iii) fermenting said red clover extract with said one or more lactic acid bacteria species, and
iv) obtaining a fermented red clover extract.

The present invention further relates to a method of making a fermented red clover extract comprising the steps of
i) providing a red clover biomass
ii) providing one or more lactic acid bacteria species
iii) fermenting said red clover biomass with said one or more lactic acid bacteria species,
iv) pressure of said red clover biomass and
v) obtaining a fermented red clover extract.

Instead of providing one or more lactic acid bacteria fermented dandelion extract can be used. Accordingly, the one or more lactic acid bacteria mentioned anywhere in this application can be replaced with fermented dandelion extract. The fermented dandelion extract can be used for fermentation of the red clover extract.

The red clovers can be any species of red clover such as one or more species of red clover selected from the group consisting of *Trifolium pratense pratense, Trifolium pratense americanum, Trifolium pratense frigidum, Trifolium pratense maritimum, Trifolium pratense parviflorum, Trifolium pratense sativum*, and *Trifolium pratense villosum*.

The dominating isoflavone in red clover is often Formononetin. In one preferred embodiment the red clover has a high content of Formononetin such as a content of Formonetin selected from the group consisting of at least 20 (weight percent), at least 22 (weight percent), at least 24 (weight percent), at least 26 (weight percent), at least 28 (weight percent), at least 30 (weight percent), at least 32 (weight percent), at least 34 (weight percent), at least 36 (weight percent), at least 38 (weight percent), at least 40 (weight percent), at least 42 (weight percent), at least 44 (weight percent), at least 46 (weight percent), at least 48 (weight percent), at least 50 (weight percent), at least 60 (weight percent), at least 65 (weight percent), at least 70 (weight percent), at least 80 (weight percent), and at least 90 (weight percent). This weight percent is defined as the weight of the Formononetin compared to the total weight of isoflavones.

Examples of red clover species with a high content of Formononetin are *Nordi* (36 weight percent) and *Pawera*. The one or more species of red clover are harvested and added to any suitable container for storage.

The red clovers are optionally heated for a defined time in order to facilitate extraction of the red clover extract. In one embodiment the temperature is increased to about 70° C. for 1 hour.

The temperature that facilitates the extraction can in another embodiment be increased to a temperature within any of the temperature intervals selected from the group consisting of for example from 4° C. to 8° C., such as from 8° C. to 10° C., for example from 10° C. to 15° C., such as from 15° C. to 20° C., for example from 20° C. to 25° C., such as from 25° C. to 30° C., for example from 30° C. to 35° C., such as from 35° C. to 40° C., for example from 40° C. to 45° C., such as from 45° C. to 50° C., for example from 50° C. to 55° C., such as from 55° C. to 60° C., for example from 60° C. to 65° C., such as from 65° C. to 70° C., for example from 70° C. to 75° C., such as from 75° C. to 80° C., for example from 80° C. to 85° C., such as from 85° C. to 90° C., for example from 90° C. to 95° C., such as from 95° C. to 100° C., or any combination of these intervals.

The time for heating of the red clovers can be any time interval such as a time interval selected from the group consisting of for example from about 15 minutes to about 30 minutes, such as from about 30 minutes to about 45 minutes, for example from about 45 minutes to about 60 minutes, such as from about 1 hour to about 2 hours, for example from about 2 hours to about 3 hours, such as from about 3 hours to about 4 hours, for example from about 4 hours to about 5 hours, such as from about 5 hours to about 10 hours, for example from about 10 hours to about 15 hours, such as from about 15 hours to about 24 hours, or more than 24 hours or any combination of these time intervals.

The liquid from the red clovers—i.e. the red clover extract—is extracted from the red clovers e.g. by compression of the red clovers or any other suitable means. The red clover extract can optionally be transferred to a separate container. The red clover extract can e.g. be kept at 3-5° C. This storage can be for longer or shorter time such as hours, days, weeks, months or years.

After storage of the liquid from the red clovers—i.e. the red clover extract—it can optionally later be heated from the low storage temperature such as from 3 to 5° C. to a higher temperature to complete the fermentation. This higher temperature can e.g. be from for example from 8° C. to 10° C., such as from 10° C. to 12° C., from for example from 12° C. to 14° C., such as from 14° C. to 16° C., from for example from 16° C. to 18° C., such as from 18° C. to 20° C., from for example from 20° C. to 22° C., such as from 22° C. to 24° C., from for example from 24° C. to 26° C., such as from 26° C. to 28° C., from for example from 28° C. to 30° C. or any combination of these intervals.

The time for completion of the fermentation e.g. at a higher temperature as indicated herein above can be selected from less than a week, 1 to 2 weeks, 2 to 3 weeks, 3 to 4 weeks, less than a months, 1 to 2 months and more than 2 months.

The temperature can be changes during the fermentation.

Lactic acid bacteria (LAB) are added to the red clover extract. The one or more lactic acid bacteria can be selected from the group consisting of *Lactobacillus* and *Bifidobacterium* species.

Of the more than 100 *Lactobacillus* species, the following are commonly used *L. acidophilus, L. fermentum, L. paracasei, L. brevis, L. gasseri, L. plantarum, L. bulgaricus, L. helveticus, L. reuteri, L. casei, L. jensenii, L. rhamnosus, L. crispatus, L. johnsonii* and *L. salivarius*.

*Bifidobacterium* has a habitat that overlaps with LAB, and it has a metabolism that produces lactic acid as a primary end-product of fermentation. Accordingly, we LAB also refer to *Bifidobacterium* in this patent application. Among 30 species of *Bifidobacterium*, the following can be most preferred: *B. adolescentis, B. breve, B. longum, B. animalis, B. infantis, B. thermophilum, B. bifidum* and *B. lactis*

Dandelion extract can optionally be added to the red clover extract before or after the fermentation process starts. In one embodiment the Dandelion extract and the one or more lactic acid bacteria are added simultaneously.

The red clover extract will be allowed to be fermented for a given time such as e.g. 6 months.

The fermentation time can also be selected from the group of time intervals consisting of from about 2 weeks to about 4 weeks, for example from about 1 month to about 2 months, from about 2 months to about 3 months, for example from about 3 months to about 4 months, from about 4 months to about 5 months, for example from about 5 months to about 6 months, from about 6 months to about 7 months, for example from about 7 months to about 8 months, from about 8 months to about 9 months, for example from about 9 months to about 10 months, from about 10 months to about 11 months, for example from about 11 months to about 12 months, from about 12 months to about 18 months, for example from about 18 months to about 24 months, or more than 24 months or any combination of these time intervals.

The fermentation temperature can be changed one or more times during the fermentation. In one embodiment the fermentation is performed at 22° C. to 25° C. for e.g. 2 to 3 days and subsequently at 15° C. to 17° C. for e.g. 2 to 3 weeks—e.g. followed by cooling of the red clover extract e.g. to 3 to 5° C. In another example the fermentation is performed at 20° C. to 24° C. for e.g. 2 to 5 days and subsequently at 15° C. to 20° C. for e.g. 2 to 3 weeks—e.g. followed by cooling of the red clover extract e.g. to 3 to 5° C.

During this fermentation period the red clover extract can optionally be transferred to a new container with certain intervals such as about every 1 to 2 weeks, every 2 to 4 weeks, every 4 to 6 weeks, every 6 to 8 weeks, every 8 to 10 weeks, every 10 to 12 weeks etc.

The fermentation is in a preferred embodiment performed at a temperature of from about 3° C. to about 5° C.

In another embodiment the fermentation is performed in a temperature interval selected from the group consisting of such as from about 0° C. to about 2° C., such as from about 2° C. to about 4° C., for example from about 4° C. to about 6° C., such as from about 6° C. to about 8° C., for example from about 8° C. to about 10° C., such as from about 10° C. to about 12° C., for example from about 12° C. to about 14° C., such as from about 14° C. to about 16° C., for example from about 16° C. to about 18° C., such as from about 18° C. to about 20° C., for example from about 20° C. to about 25° C., such as from about 25° C. to about 30° C., for example from about 30° C. to about 40° C., such as from about 40° C. to about 50° C., for example from about 50° C. to about 60° C., such as from about 60° C. to about 70° C., or more than 70° C. or any combination of these intervals.

The temperature for the fermentation must not exceed a temperature that will kill the lactic acid bacteria. For certain lactic acid bacteria this means that the fermentation temperature must be below 50° C.

The pH of the red clover extract will decrease to about 4 or less than 4 during the fermentation process. The decrease of the pH results in conservation of the red clover extract.

The pH of the red clover extract after fermentation can in one embodiment be selected from group consisting of the pH intervals of from about pH 1 to about pH 1.5, for example from about pH 1.5 to about pH 2, such as from about pH 2 to about pH 2.5, for example from about pH 2.5 to about pH 3, such as from about pH 3 to about pH 3.5, for example from about pH 3.5 to about pH 4, such as from about pH 4 to about pH 4.5, for example from about pH 4.5 to about pH 5, such as from about pH 5 to about pH 5.5, for example from about pH 5.5 to about pH 6, such as from about pH 6 to about pH 6.5, for example from about pH 6.5 to about pH 7, or a pH higher than 7 or any combination of these intervals.

In one preferred embodiment the pH of the red clover extract after fermentation is below 5, such as below 4.5, such as below 4, such as below 3.5, such as below 3, such as below 3.5, such as below 3, such as below 2.5, such as below 2, such as below 1.5 or such as below 1.

The red clover extract will subsequently be stable for a long period of time such as more than 3 months, more than 6 months, more than 9 months, more than 1 year, more than 1.5 years, more than 2 years, more than 3 years, more than 4 years or more than 5 years. In one embodiment it is not necessary to add preservative(s) to the final product.

The concentration of the isoflavones in the final product can e.g. be increased by
1) Selection of red clover with a high isoflavone content as the starting material and/or
2) Selection of conditions for growth of the red clover resulting in an increased isoflavone content in the red clover starting material and/or
3) Use of extractions methods that increases the content of isoflavones in the extract and/or
4) Up-concentration of the isoflavones in the extract by freeze-drying and/or lyophilization and/or evaporation based techniques and/or osmosis based techniques and/or precipitation techniques The active components in the red clover extract can be concentrated using reverse osmosis. In order to preserve isoflavones, flavonoids, isoflavonoids and phenolics from degradation during processing the temperature of the extract can be kept below 40-50° C. Pressure on the other hand can be less crucial and an operation pressure of up to 35 bar can be used.

Concentration of isoflavonoids from ethanol extracts from dried red clover flowers using reverse osmosis have been performed by Xu et al (2006) [L. Xu, A. Kumar, K. Lamb and L. Layton: *Recovery of isoflavoids from red clover flowers by membrane-based process*, Innovative Food Science and Emerging Technologies, Volume 7, (2006), Pages 251-256]. They reported a volume reduction of 10-15 times for their extract, but also a loss of nearly 15-20% of the isoflavonoids fed to their reverse osmosis membrane unit. This method can be used for concentration of isoflavones in the composition according to the present invention.

Though results for red clover extract (aqueous solution) concentration using reverse osmosis has not been found in the literature, experiments with aqueous willow extracts show, that no significant loss of flavonoids occur during reverse osmosis concentration (Christensen et al, 2012) [K. V. Christensen, M. L. Ohm, V. G. Horn: *Towards a Membrane Process based Parth to Concentrate Willow Extract*, Procedia Engineering, Volume 44, 2012, Pages 1736-1738]. The main reason for this discrepancy is most likely, that ethanol partly dissolve the reverse osmosis membrane making it permeable for isoflavonoids, while water does not, thus maintaining the membrane impermeable to flavonoids and therefore also isoflavonoids. Reverse osmosis concentration can be used to concentrate the isoflavones in the composition according to the present invention.

Fresh red clover extract can e.g. have a total drymatter content, organic and inorganic, of around 6.6%-weight and an ash content around 1.5%-weight. Based on this information, the results of Christensen et al (2012), and a maximum operating pressure of 35 bar, reverse osmosis will be able to produce a concentrate with a drymatter content around 10-12%-weight total drymatter, without any significant loss of isoflavones, flavonoids, isoflavonoids, phenolics, carbohydrates and salts.

Fermented red clover extract can e.g. have a total drymatter content, organic and inorganic, of around 3.0%-weight and an ash content around 1.0%-weight. Based on this information, the results of Christensen et al (2012), and a maximum operating pressure of 35 bar, reverse osmosis will be able to produce a concentrate with a drymatter content around 12-15%-weight total drymatter, without any significant loss of isoflavones, flavonoids, isoflavonoids, phenolics, carbohydrates and salts.

The red clover extract can—either before or after fermentation—be concentrated by vacuum evaporation to increase the concentration of isoflavones. Vacuum evaporation at low pressure is preferred, wherein the temperature does not exceed 30-40 degrees Celsius, or 40-50 degrees Celsius, or 50-60 degrees Celsius or 60-70 degrees Celsius. This method can concentrate the extract to about 40% dry matter or a dry matter content selected from the group consisting of 10-20% dry matter, 20-30% dry matter, 30-40% dry matter or 40-50% dry matter, or any combination of these intervals.

The red clover extract can—either before or after fermentation—be freeze dried to a powder containing 1-10% water, such as less than 10%, such as less than 9%, such as less than 8%, such as less than 7%, such as less than 6%, such as less than 5%, such as less than 4%, such as less than 3%, such as less than 2% or such as less than 1% water. The extract is e.g. dried at a temperature selected from the group consisting of 30-40 degrees Celsius, 40-50 degrees Celsius, 50-60 degrees Celsius, or any combination of these intervals.

The composition according to the present invention can be in one embodiment be pasteurized.

Product

Phytoestrogen compounds according to the present invention are defined as naturally occurring plant substances, said substances being either structurally or functionally similar to 17β-estradiol or generating estrogenic effects. Phytoestrogens consist of a number of classes including isoflavones, coumestans, lignans and resorcylic acid lactones. Examples of isoflavones according to the present invention are genistein, daidzein, formononetin, ononin, biochanin A, and sissotrin.

The phytoestrogen compounds of a composition according to the present invention are preferably isoflavones, more preferably genistein, daidzein, formononelin, ononin, Biochanin A and/or sissotrin. A preferred composition according to the present invention may accordingly comprise a single isoflavone, such as genistein, daidzein, formononelin, ononin, Biochanin A or sissotrin, or it may comprise at least one isoflavone selected from the group consisting of at least genistein, daidzein, formononelin, ononin, Biochanin A and/or sissotrin or any combination of these isoflavones. The composition can comprise more than one isoflavone e.g. selected from the group consisting of at least genistein, daidzein, formononelin, ononin, Biochanin A and sissotrin or any combination of these isoflavones.

When present in the plant the isoflavones are mainly in a glucoside form, i.e. attached to a sugar molecule. This glucoside form can be deconjugated to yield a so-called aglycone form, which is the biologically active species. A composition according to the present invention may comprise isoflavones in glucoside and/or aglycone forms regardless of whether the deconjugation to the aglycone form has taken place biologically, in vitro or by any other means whereby the isoflavones are included in a composition according to the present invention or if the aglycone forms are the native form of the isoflavones. Preferably the majority of the isoflavones are in the aglycone form such as more than 80%, more than 90%, more than 95% or more than 99%.

The red clover extracts contain or comprise different percentages of isoflavones including genistein, daidzein, formononelin, ononin, Biochanin A and/or sissotrin such as the percentages of isoflavones listed elsewhere herein.

The present invention relates in one aspect to one or more of the following compositions:

A composition comprising a red clover extract and one or more lactic acid bacteria species.

A composition comprising isoflavones isolatable from red clover and one or more lactic acid bacteria species.

A composition comprising a red clover extract obtainable by contacting the red clover extract with one or more lactic acid bacteria species.

A composition comprising red clover aglycone isoflavones and essentially no glycone isoflavones, wherein said composition is obtainable by a method comprising the steps of providing, processing and fermenting red clover with one or more lactic acid bacteria species.

A composition comprising a red clover extract obtainable by a method comprising the steps of
  i) providing a red clover extract
  ii) providing one or more lactic acid bacteria species
  iii) fermenting said red clover extract with said one or more lactic acid bacteria species, and
  iv) obtaining a fermented red clover extract.

A composition comprising aglycone isoflavones isolatable from red clover and essentially no glycosylated isoflavones.

A composition comprising aglycone isoflavones isolatable from red clover and essentially no glycosylated isoflavones and essentially no saccharide residues resulting from the cleavage of said saccharide residues from the glycone form of said isoflavones.

The composition according to any of the bullet points above, wherein an aqueous extract of Dandelion is added to the composition.

The composition according to any of the bullet points above, wherein more than at least 90% of the isoflavones are on an aglycone form.

The composition according to any of the bullet points above, wherein the composition comprises at least one isoflavone selected from the group consisting of biochanin A and Formononetine, including a combination of both.

A composition according to any of the bullet points above for use as a medicament.

A composition according to any of the bullet points above for use of treatment of menopause-related symptoms, such as one or more of hot flashes, perspiration, and headache.

A composition according to any of the bullet points above for use of treatment of premenstrual syndrome.

A composition according to any of the bullet points above for use of treatment of osteoporosis and/or osteopenia.

A composition according to any of the bullet points above for use of treatment of arteriosclerosis.

A composition according to any of the bullet points above for use of treatment of cholesterol plaques.

A composition according to any of the bullet points above for use of treatment of hypertension.

A composition according to any of the bullet points above for use of treatment of cardiovascular diseases.

A composition according to any of the bullet points above for use of treatment of one or more cancer diseases such as treatment of B-cell precursor (BCP)-leukemia, breast cancer and colorectal cancer.

A composition according to any of the bullet points above for use of treatment of one or more skin diseases such as eczema, psoriasis and acne.

A composition according to any of the bullet points above for use of treatment of one or more respiratory diseases such as cough, asthma and bronchitis.

A composition according to any of the bullet points above for use of treatment of emotional distress including mood swings, dysphoria, dysthymia and/or depression. The emotional distress can e.g. be related to menopause and/or PMS.

In one aspect the present invention provides a composition comprising (a) at least one phytoestrogen such as at least one isoflavone, and (b) at least one lactic acid bacteria and/or fermented dandelion extract and (c) optionally dandelion juice.

The composition according to the present invention can also comprise Metformin or be given in combination with treatment with Metformin for treatment of Type 2 diabetes.

The composition according to the present invention can also comprise D-vitamin and/or $Ca^{2+}$ and/or magnesium or be given in combination with treatment with D-vitamin and/or $Ca^{2+}$ and/or magnesium e.g. for treatment of Osteoporosis, Osteopenia or other bone related diseases or bone related conditions.

The composition according to the present invention can be administered to an individual in need thereof such as a human being in need thereof together with administration of D vitamin (simultaneously or subsequently in order). The daily dose of D vitamin can be selected from the group consisting of 20 µg/day, 25 µg/day, 30 µg/day, 35 µg/day, 40 µg/day, 50 µg/day, and 60 µg/day. The daily dose of D vitamin can alternatively be selected from the group consisting of 20-22 µg/day, 22-24 µg/day, 24-26 µg/day, 26-28 µg/day, 28-30 µg/day, 30-32 µg/day, 32-34 µg/day, 34-36 µg/day, 36-38 µg/day, 38-40 µg/day, 40-42 µg/day, 42-44 µg/day, 44-46 µg/day, 46-48 µg/day, 48-50 µg/day, 50-60 µg/day, and more than 60 µg/day or any combination of these intervals.

The composition according to the present invention can be administered to an individual in need thereof such as a human being in need thereof together with administration of calcium (simultaneously or subsequently in any order). The daily dose of calcium can be selected from the group consisting of 400 mg/day, 500 mg/day, 600 mg/day, 700 mg/day, 800 mg/day, 900 mg/day, 1000 mg/day, 1100 mg/day, 1200 mg/day, 1300 mg/day, 1400 mg/day and 1500 mg/day. The daily dose of calcium can alternatively be selected from the group consisting of 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-2000 mg/day, 2000-2500 mg/day, 2500-3000 mg/day, 3000-4000 mg/day, and more than 4000 mg/day or any combination of these intervals.

The composition according to the present invention can be administered to an individual in need thereof such as a human being in need thereof together with administration of D vitamin (simultaneously or subsequently in order) and calcium (simultaneously or subsequently in order). The daily dose of D vitamin can be selected from the group consisting of 20 µg/day, 25 µg/day, 30 µg/day, 35 µg/day, 40 µg/day, 50 µg/day, and 60 µg/day. The daily dose of D vitamin can alternatively be selected from the group consisting of 20-22 µg/day, 22-24 µg/day, 24-26 µg/day, 26-28 µg/day, 28-30 µg/day, 30-32 µg/day, 32-34 µg/day, 34-36 µg/day, 36-38 µg/day, 38-40 µg/day, 40-42 µg/day, 42-44 µg/day, 44-46 µg/day, 46-48 µg/day, 48-50 µg/day, 50-60 µg/day, and more than 60 µg/day or any combination of these intervals. The daily dose of calcium can be selected from the group consisting of 400 mg/day, 500 mg/day, 600 mg/day, 700 mg/day, 800 mg/day, 900 mg/day, 1000 mg/day, 1100 mg/day, 1200 mg/day, 1300 mg/day, 1400 mg/day and 1500 mg/day. The daily dose of calcium can alternatively be selected from the group consisting of 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-2000 mg/day, 2000-2500 mg/day, 2500-3000 mg/day, 3000-4000 mg/day, and more than 4000 mg/day or any combination of these intervals. The composition according to the present invention can be administered to an individual in need thereof such as a human being in need thereof together with administration of magnesium (simultaneously or subsequently in any order). The daily dose of magnesium can be selected from the group consisting of 100 mg/day, 200 mg/day, 300 mg/day, 400 mg/day, 500 mg/day, 600 mg/day, 700 mg/day, 800 mg/day, 900 mg/day, 1000 mg/day, 1100 mg/day, 1200 mg/day, 1300 mg/day, 1400 mg/day and 1500 mg/day. The daily dose of magnesium can alternatively be selected from the group consisting of 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-2000 mg/day, 2000-2500 mg/day, 2500-3000 mg/day, 3000-4000 mg/day, and more than 4000 mg/day or any combination of these intervals.

The composition according to the present invention can be administered to an individual in need thereof such as a human being in need thereof together with administration of a mixture of vitamins (simultaneously or subsequently in any order).

The composition according to the present invention can comprise D vitamin and/or one or more other vitamins and/or calcium and/or magnesium and/or boron.

The composition according to the present invention can also comprise Bisphosphonates or be given in combination with treatment with Bisfosfonates for treatment of Osteoporosis.

Isoflavones from red clover may increase production of osteoprotegerin (OPG). OPG is a secreted decoy receptor for RANKL, which is expressed by stromal/osteoblast cells, and RANKL is essential for the maturation and activity of osteoclasts. OPG inhibits osteoclastogenesis by preventing the interaction between RANKL-RANK. OPG-deficient mice exhibit severe trabecular and cortical bone porosity, with enhanced osteoclastic bone resorption. Thus, the balance between the expression of OPG and RANKL equalizes bone formation and resorption during bone remodeling. Isoflavones from red clover may exerts a positive effect on the bones, not only by increasing osteoblast formation and/or osteoblastic activities, but also by suppressing osteoclast formation and bone resorption in vitro and in vivo. Furthermore, the isoflavones from red clover may decrease the ratio of RANKL/OPG mRNA expression. Therefore, isoflavones can have a stimulatory effect on bone formation via increased osteogenic differentiation and inhibited adipogenic and osteoclastic differentiation, resulting in increase in bone mass.

The composition according to the present invention can also comprise one or more Statins or be given in combination with treatment with one or more Statins for treatment of dyslipidemia. Examples of statins are given in the table herein below.

| Name of drug | Supplier | Statin |
| --- | --- | --- |
| Atorvastatin "Actavis" | Actavis Group | Atorvastatin |
| Atorvastatin "Bluefish" | Bluefish | Atorvastatin |
| Atorvastatin "Hexal" | Hexal | Atorvastatin |
| Atorvastatin "Krka" | KRKA Sverige | Atorvastatin |
| Atorvastatin "Orifarm" | Orifarm Generics | Atorvastatin |
| Atorvastatin "Pfizer" | Pfizer | Atorvastatin |
| Atorvastatin "Sandoz" | Sandoz | Atorvastatin |
| Atorvastatin "Stada" | Stada | Atorvastatin |
| Atorvastatin "Tabs n Caps" | Parallelimport | Atorvastatin |
| Atorvastatin "Teva" | TEVA | Atorvastatin |
| Crestor ® | AstraZeneca | Rosuvastatin |
| Fluvastatin "2care4" | Parallelimport | Fluvastatin |
| Fluvastatin "Stada" | Stada | Fluvastatin |
| Fluvastatin "Teva" | TEVA | Fluvastatin |
| Lescol XL | Parallelimport | Fluvastatin |
| Lescol ® | Novartis | Fluvastatin |
| Lipitor | Parallelimport | Atorvastatin |
| Lovastatin "Actavis" | Actavis | Lovastatin |
| Perichol | PharmaCoDane | Simvastatin |
| Pravastatin "2care4" | Parallelimport | Pravastatin |
| Pravastatin "Arrow" | Arrow Generics | Pravastatin |
| Pravastatin "Sandoz" | Sandoz | Pravastatin |
| Pravastatin "Stada" | Stada | Pravastatin |
| Pravastatinnatrium "Teva" | TEVA | Pravastatin |
| Simestat | Parallelimport | Rosuvastatin |
| Simvastatin "Actavis" | Actavis Group | Simvastatin |
| Simvastatin "Arrow" | Arrow Generics | Simvastatin |
| Simvastatin "Bluefish" | Bluefish | Simvastatin |
| Simvastatin "Hexal" | Hexal | Simvastatin |
| Simvastatin "KRKA" | KRKA Sverige | Simvastatin |
| Simvastatin "Orifarm" | Orifarm Generics | Simvastatin |
| Simvastatin "Orion" | Orion Pharma | Simvastatin |
| Simvastatin "Pfizer" | Pfizer | Simvastatin |
| Simvastatin "Sandoz" | Sandoz | Simvastatin |
| Simvastatin "Teva" | TEVA | Simvastatin |
| Tahor | Parallelimport | Atorvastatin |
| Visacor ® | Parallelimport | Rosuvastatin |
| Zarator ® | Pfizer | Atorvastatin |
| Zocor ® | MSD | Simvastatin |

The composition according to the present invention can in one embodiment comprise one or more sweetener(s) such as *Stevia*.

A composition according to the present invention may optionally comprise a carbohydrate source, and/or a fat source, and/or one or more flavouring agents such as licorice root, berry juice (e.g. from blackcurrants), flower juice (e.g. from elderflowers), fruit juice (e.g. from oranges) and/or one or more vitamins such as vitamin D, and/or one or more minerals such as calcium, and/or one or more electrolytes, and/or one or more trace elements and/or one or more other conventional additives such as magnesium. The nutritional composition according to the present invention may in one embodiment also comprise one or more flavouring agents such as cocoa, vanilla, lime, strawberry or soup flavours, such as mushroom, tomato or bouillon, and/or and sweeteners such as aspartame as well as other additives such as xanthan gum. The composition according to the present invention can also comprise one or more fruit juices such as apple juice, orange juice and pineapple juice.

When a carbohydrate source is present in a composition according to the present invention, it is preferably present in an amount of less than 30 weight percent such as less than 25 weight percent of the composition. Preferably, the amount of carbohydrate amounts to at least 5 weight percent, more preferred at least 10 weight percent, and most preferred at least 15 weight percent, of the composition. In one embodiment the carbohydrate source is present in the composition according to the present invention in an amount selected from the group consisting of from 1 to 2 g/100 g red fermented clover extract, from 2 to 4 g/100 g red fermented clover extract, from 4 to 8 g/100 g red fermented clover extract, from 8 to 12 g/100 g red fermented clover extract, from 12 to 16 g/100 g red fermented clover extract, and from 16 to 20 g/100 g red fermented clover extract.

Lecithinated fat reduced cacao is particularly preferred. Other preferred carbohydrates for use in a composition according to the present invention are polydextrose or saccharose, but these should be limited using other sweeteners like e.g. aspartame.

When a fat source is present in a composition according to the present invention, it is usually present in an amount from 0.1 to 5 weight percent, such as from 0.1 to 0.5 weight percent, for example from 0.5 to 1 weight percent, such as from 1 to 2 weight percent, for example from 2 to 3 weight percent, such as from 3 to 4 weight percent, for example from 4 to 5 weight percent, or any combination of these intervals. The fat source will preferably comprise polyunsaturated fatty acids and monounsaturated fatty acids and optionally also saturated fatty acids. Soy lecithins and α-linolenic acids are particularly preferred. The amount of polyunsaturated fatty acids and monounsaturated fatty acids, including the essential fatty acids, may range from 35 to 50, preferably 38 to 44, weight percent of the total amount of the fat source. The essential fatty acids are also called omega-6 and omega-3 fatty acids and include linolic acid and/or linolenic acid (α-linolenic acid). The amount of saturated fatty acids may be from 20 to 30 weight percent, preferably 22 to 26 weight percent, of the total amount of fat.

When a protein source is present in a composition according to the present invention, it is usually present in an amount from 0.1 to 5 weight percent, such as from 0.1 to 0.5 weight percent, for example from 0.5 to 1 weight percent, such as from 1 to 2 weight percent, for example from 2 to 3 weight percent, such as from 3 to 4 weight percent, for example from 4 to 5 weight percent, or any combination of these intervals.

Vitamins and minerals may optionally be added to a composition according to the present invention in accordance with the limits laid down by health authorities. The vitamins will typically include A, B1, B2, B12, folic acid, niacin, panthotenic acid, biotin, C, D, E and K. The minerals will typically include iron, zinc, iodine, copper, manganese, chromium and selenium. Electrolytes, such as sodium, potassium and chlorides, trace elements and other conventional additives may also be added in recommended amounts.

The composition according to the present invention can comprise one or more of the following ingredients:

| Ingredient | Content per 100 g fermented red clover extract |
| --- | --- |
| Energy | From 50 KJ to 100 KJ such as 80 KJ (20 kcal) |
| Protein | From 0 to 1 g such as 0.5 g |
| Carbohydrate | From 1 to 5 g such as 2.5 g |
| Fat | From 0 to 1 g such as 0.5 g |
| Organic acid | From 0 to 1 g such as 0.5 g |
| Sodium | From 0.001 to 0.01 g such as 0.0067 g |
| Salt (2.5 x sodium) | From 0.01 to 0.1 g such as 0.01675 g |
| Water | From 80 to 97 g such as 96.6 g |
| Ash | From 0.1 to 1 g such as 0.6 g |

A composition according to the present invention may be used as a food for special dietary use, preferably for lowering serum levels of glucose and/or for lowering serum levels of insulin and/or for lowering total serum cholesterol and/or LDL-cholesterol and/or triglyceride levels and/or for increasing glucose tolerance and/or insulin sensitivity and/or for preventing and/or alleviating and/or treating impaired glucose tolerance and/or insulin secretory failure in diabetic subjects and/or for preventing and/or alleviating and/or treating an arteriosclerotic condition by reducing the influx of lipoproteins and/or cholesterol and/or triglycerides into the endocelium of the arterial wall of a diabetic subject suffering from a cardiovascular disease. For example, from one to three daily meals of ordinary food can be supplemented or replaced by a composition according to the present invention. Hereby, significant reductions in serum levels of total cholesterol and LDL-cholesterol and triglyceride can be obtained, as well as an improvement of HDL/LDL-cholesterol ratio and/or an increase in serum HDL-cholesterol levels.

In one embodiment the present invention provides a composition according to the present invention for use as a medicament or as a dietary preparation. The present invention also provides the use of a composition according to the present invention for the manufacture of a medicament for preventing, alleviating and/or treating the medical indication described elsewhere herein.

A composition according to the present invention for use as a medicament and/or the use of a composition according to the present invention for the manufacture of a medicament for treating a subject with menopausal symptoms including hot flashes and/or osteoporosis and/or diabetes and/or the metabolic syndrome and/or a cardiovascular disease associated therewith may be effective in i) lowering serum glucose levels and/or ii) reducing the influx of cholesterol and/or triglycerides into the arterial wall and/or the amount of oxidized LDL-cholesterol present in the arterial wall and/or iii) lowering total serum cholesterol and/or serum LDL-cholesterol and/or serum triglyceride levels and/or serum homocystein levels and/or increasing the HDL/LDL-cholesterol ratio and/or serum HDL-cholesterol levels and/or iv) increasing glucose tolerance and/or insulin sensitivity and/or v) alleviating impaired glucose tolerance and/or insulin secretory failure and/or vi) preventing, alleviating, eliminating and/or treating cardiovascular diseases, such as e.g. hypertriglyceridaemia, hypercholesterolaemia, arteriosclerosis, atherosclerosis, arteriolosclerosis, angina pectoris, thrombosis, myocardial infarction, hypertension, hyperglycaemia, and hyperinsulinaemia, in a diabetic subject.

A composition according to the present invention for use as a medicament and/or the use of a composition according to the present invention for the manufacture of a medicament may also be effective in treating cardiovascular diseases such as e.g. fatty streak formation and/or fibrous plaque development and/or complicated lesion development. Furthermore, a composition according to the present invention for use as a medicament and/or the use of a composition according to the present invention for the manufacture of a medicament may also be effective in treating a procoagulant state and/or an increased activity of clotting factors, insulin resistance, glycosidation and/or oxidation and/or chemical modification of lipoproteins, as well as impaired glucose tolerance.

In one embodiment the present invention provides a pharmaceutical preparation comprising a composition according to the present invention. The pharmaceutical preparation can be prepared in any way known to the skilled person.

Formulation and Administration

The composition according to the present invention can e.g. be formulated as a pill, capsule, gel, mixture, liquid composition, liquid mixture, powder or any other suitable formulation.

A composition according to the present invention can be part of a functional food product such as a liquid functional food product (e.g. a fruit juice), a semi-solid food product (e.g. an yoghurt) or a solid food product (e.g. an energybar).

A composition according to the present invention can be part of a dietary supplement.

The composition according to the present invention can be administered using the following routes of administration and form of drug.

In one embodiment per-orally intake is preferred—e.g. intake in the form of pills, capsules, powder, liquid mixture, liquid composition, liquid extract or gel form.

In another aspect intake by injection is preferred—i.e. systemic or local injections.

Other forms of administration comprises Jet-infusion (micro-drops, micro-spheres, micro-beads) through skin, inhalation, nose-drops, eye-drops, ear-drops, skin application as ointment, gel or lotion, vaginal application as ointment, gel, crème or washing, Gastro-Intestinal flushing, rectal washings or by use of suppositories.

The drug treatment can be performed as single intake, injection, application, washing and/or multiple intake, injection, application, washing—either on single day basis or over prolonged time as days, month, years. Drug dose and regimen can be modified during the course.

Treatment

Any treatment mentioned herein below can be ameliorating, curative or prophylactic.

Menopausal Symptoms

Menopausal symptoms are a common phenomenon causing discomfort to many middle aged women throughout the world. The composition according to the present invention can be used to treat and/or ameliorate one or more menopausal symptoms. The core symptoms are experienced as hot flushes (HF), night sweats, vaginal dryness and sleep disturbance. Other generally reported secondary symptoms are sexual dysfunction, depression, anxiety, memory loss, fatigue, headache, joint pains and weight gain. Osteoporosis, cardiovascular risk and negative changes in lipid profile are also commonly associated with the reductions in estrogen during and post menopause and can be treated by the composition according to the present invention.

The composition according to the present invention can be used for treatment of the premenstrual syndrome and menopause-related symptoms such as hot flashes, perspiration, headache and osteoporosis.

Osteoporosis and Osteopenia

The composition can also be used for protecting men and/or women against osteoporosis.

The treatment can result in maintaining the bones healthy with a satisfactory bone density. The treatment can inhibit the osteoporosis and/or result in improvement/increase of the bone density.

Osteopenia refers to bone mineral density (BMD) that is lower than normal. Osteopenia can be defined as a T score between −1 and −2.5. Osteoporosis can be defined as a T score equal to or <2.5. The composition according to the present invention can be used for treatment and or inhibition of Osteopenia and/or osteoporosis.

Type 2 Diabetes, Metabolic Syndrome and Cardiovascular Diseases

A composition according to the present invention represents a new approach to treatment of type 2 diabetes and is believed to be capable of i) lowering serum levels of glucose, and/or ii) lowering serum levels of insulin, and/or iii) lowering total serum cholesterol and/or LDL-cholesterol and/or triglyceride levels, and/or iv) increasing glucose tolerance and/or insulin sensitivity and/or v) preventing and/or alleviating and/or treating impaired glucose tolerance and/or insulin secretory failure in diabetic subjects and/or vi) preventing and/or alleviating and/or treating an arteriosclerotic condition by reducing the influx of cholesterol and/or triglycerides into the endocelium of the arterial wall of a diabetic subject suffering from a cardiovascular disease.

A composition according to the present invention may be effective in treating and/or preventing type 2 diabetes and/or the metabolic syndrome and/or reducing and/or eliminating one or more of the risk factors for cardiovascular diseases associated with diabetes and/or the metabolic syndrome. Accordingly, a composition according to the present invention may be effective in preventing, alleviating and/or treating conditions such as e.g. increased serum levels of glucose, hypertriglyceridaemia, hypercholesterolaemia, hypertension, and hyperinsulinaemia in diabetic individuals. A composition according to the present invention may also be capable of reducing, preventing and/or eliminating fatty streak formation and/or fibrous plaque development and/or effective in mediating a regression of one or both of said arteriosclerotic conditions.

A composition according to the present invention may be effective in reducing insulin resistance by stimulating cells or receptors located thereon that are normally stimulated by insulin, but less sensitive to the hormone in a subject diagnosed with type 2 diabetes and/or the metabolic syndrome. A composition according to the present invention may also be effective in stimulating cells comprising a beta-2-adrenergic receptor or a receptor belonging to the class of beta-2-adrenergic receptors. The final phase of type 2 diabetes development is characterised by insulin secretory failure (ISF), and in one presently preferred hypothesis, this failure is at least preventable by a composition according to the present invention effective in stimulating insulin secretion.

Both plasma triglyceride and lipoprotein levels are usually increased in individuals treated for type 2 diabetes and/or the metabolic syndrome, and these increased levels, unless reduced by treatment, are likely to lead to coronary heart disease (CHD). Beta-2-adrenergic receptors are present on many different types of cells including fat cells. The beta-2-adrenergic receptor is involved in the regulation of triglyceride synthesis in fat cells and according to one presently preferred hypothesis, binding of soy peptides and/or a phytoestrogen compound such as e.g. a naturally occurring isoflavone to a beta-2-adrenergic receptor present on a fat cell or in an arterial wall is effective in reducing e.g. the synthesis of triglycerides in fat cells and/or the release of triglycerides into the blood stream and/or reducing the influx of triglycerides into the arterial wall.

Hypertriglyceridaemia in diabetes has been associated with a variety of changes in circulating lipoproteins, and a composition according to the present invention may be capable of preventing, treating, alleviating and/or eliminating cardiovascular risk factors such as e.g. chylomicronaemia, an increased level of VLDL, an increased level of remnants (VLDL and chylomicrons), and LDL and HDL containing increased levels of triglycerides.

Lipoprotein fractions obtained from type 2 diabetic subjects tend to lose their typical sharp LDL peak and instead have a broad diffuse LDL band termed polydisperse LDL. Dissection of polydisperse LDL reveals that diabetics have an increased serum level of intermediate-density-lipoprotein (IDL), an abnormal LDL peak, and an increase in the amount of small dense LDL. While small dense LDL particles have been associated with CHD in the general population, a similar association in diabetes remains to be established. Accordingly, a composition according to the present invention may be effective in promoting a decreased serum level of intermediate density lipoprotein (IDL), a normal, sharp LDL peak, and a decreased amount of small dense LDL.

Accordingly, diabetic dyslipidaemia of type 2 diabetes is generally associated with abnormalities of apolipoprotein and lipoprotein particle distributions and results in increased plasma VLDL and remnant levels, an increase in the apoE concentration in VLDL and remnants, an increase in the amount of small dense LDL, and an altered HDL particle distribution.

According to one presently preferred hypothesis, a composition according to the present invention will alleviate abnormalities associated with apolipoprotein and lipoprotein particle distribution and promote a decreased plasma VLDL and remnant level, a decrease in the apoE concentration in VLDL and remnants, a decrease in the amount of small dense LDL, and a HDL particle distribution similar to that of a comparable non-diabetic, healthy individual.

Hypertriglyceridaemia in diabetes is associated with an increase in the clotting activities of thrombogenic factors such as factor VII and factor X and an increase in the level of the inhibitor of tissue plasminogen activator, PAI-1. The increased inhibitor concentration results in a decreased level of plasminogen synthesis and thus a decreased level of plasminogen stimulated clot lysis. These changes in clotting activities no doubt contribute to the observed procoagulant state in diabetes. Accordingly, the present invention provides a composition, which may be effective in normalising the clotting activities of thrombogenic factors such as factor VII and factor X by e.g. decreasing the increased activity thereof observed in a subject diagnosed as having type 2 diabetes or diagnosed as having an impaired glucose tolerance or a decreased insulin sensitivity. Also, a composition according to the present invention may be effective in promoting a decrease in the concentration of the inhibitor of tissue plasminogen activator, PAI-1, which in turn leads to an increased plasminogen stimulated clot lysis. A composition according to the present invention may also be effective in reducing an increased platelet aggregatability and/or mediating directly or indirectly a reduction of the increased level of lipoprotein (a) associated with a procoagulant state in a diabetic condition.

Hyperinsulinaemia is also considered a risk factor for coronary heart disease (CHD) in diabetic subjects due to the association of high insulin levels with increased incidence and mortality rates of CHD. A composition according to the present invention may be effective in lowering serum insulin levels in subjects diagnosed with type 2 diabetes. Diabetic patients having increased endogenous insulin levels, i.e. subjects diagnosed with type 2 diabetes, or having increased peripheral circulating insulin levels as a result of intermittent injections of large amounts of exogenous insulin are particularly prone to hyperinsulinaemia.

Hyperinsulinaemia in both normal persons, persons with the metabolic syndrome and those with type 2 diabetes appears to be related to obesity. Insulin levels are very often increased in both the fasted state and after intake of a diet rich in carbohydrates in obese individuals, irrespective of whether they suffer from a diabetic condition or not. Furthermore, hyperinsulinaemia appears to be directly correlated to the degree of obesity. Accordingly, hyperinsulinaemia is one of the many risk factors for CHD associated with obesity, and insulin may modulate many other obesity-related risk factors. Accordingly, a composition according to the present invention may be effective in lowering insulin levels in obese subjects with diabetes or the metabolic syndrome.

In obese subjects diagnosed as diabetic, LDL-particle size is independently correlated with factors such as e.g. serum triglyceride and serum insulin levels. Consequently, it is possible that the extent of adiposity and concomitant insulin resistance in hyperinsulinaemic individuals is associated with the occurrence small dense LDL, independently of hypertriglyceridaemia, which is another diabetic condition also putatively associated with small dense LDL formation. Accordingly, both insulin resistance and hyperinsulinaemia appear to play a central role in the pathogenesis of atherosclerosis in diabetes. A composition according to the present invention may be effective in alleviating and/or treating insulin resistance and/or hyperinsulinaemia.

In one embodiment the present invention provides a composition effective in reducing and/or eliminating risk factors for coronary heart disease (CHD) in obese subjects suffering from a diabetic condition and/or the metabolic syndrome. Consequently, a composition according to the present invention may be capable of preventing, alleviating, treating and/or eliminating hyperinsulinaemia and/or hyperglycaemia and/or hypertension and/or hypertriglyceridaemia and/or hypercholesterolaemia and/or effective in mediating an increase in the low serum levels of HDL-cholesterol.

It is very possible that type 2 diabetes is also associated with insulin resistance and hyperinsulinaemia independently of an increase in abdominal lipids.

Hyperinsulinaemia in turn is associated with dyslipidaemia, i.e. increased VLDL, decreased and altered HDL and increased small dense LDL, and with hypertension, all of which are risk factors for atheriosclerosis. This array of abnormalities and disorders, or a part of thereof, is generally termed the insulin resistance syndrome, or syndrome X, or metabolic syndrome.

In one embodiment, a composition according to the present invention may be capable of effectively decreasing and/or eliminating increased serum levels of VLDL and/or LDL, and/or increasing decreased serum levels of HDL, and of decreasing and/or eliminating serum LDL levels including serum levels of small dense LDL. A composition according to the present invention may also be capable of reducing an elevated level of small, dense LDL-particles and/or reducing an elevated ratio of LDL-apoB to LDL-cholesterol and/or preventing, treating or alleviating hypertension.

Hyperinsulinaemia in itself may well be capable of affecting the arterial wall either directly or indirectly by promoting or facilitating the promotion of changes similar to those leading to severe atherogenesis. Insulin may well promote both arterial smooth muscle cell proliferation and cholesterol ester accumulation in the arterial wall. A composition according to the present invention may in one embodiment be effective in preventing, alleviating, eliminating and/or treating fatty streak formation, fibrous plaque development, complicated lesion formation, thrombosis, platelet aggregation and/or myocardial infarction. A composition according to the present invention may also be capable of suppressing any effect, that would otherwise generate an increased turnover of arterial smooth muscle cells, i.e. an enhanced arterial smooth muscle cell proliferation, and/or lead to an increased cholesterol ester accumulation in the arterial wall.

Since insulin can be expected to be capable, either in combination with other compounds such as additional growth factors, or on its own, of increasing the levels of intracellular cholesterol, by e.g. increasing a delivery of LDL-cholesterol via the LDL-receptor, and concomitantly therewith increase an endogenous biosynthesis of cholesterol that makes yet more cholesterol available for new membrane synthesis in the cell proliferation process, it is an object of the present invention to counteract any increased activity including any insulin stimulated increased activity of the LDL-receptor.

It is also possible that insulin and other growth factors have the potential to promote the accumulation of cholesterol intracellularly. This may in fact well occur in a diabetic subject and more generally under conditions when cells are stimulated, but cannot proliferate normally. Accordingly, a composition of the present invention may also be capable of alleviating, eliminating and/or treating any decrease, including any insulin mediated decrease, in the HDL receptor-mediated cholesterol efflux. Accordingly, a composition according to the present invention may be capable of reducing and/or eliminating any enhanced retention of intracellular cholesterol caused by a decreasing HDL receptor-mediated cholesterol efflux.

Modifications to lipoproteins are another risk factor for cardiovascular disease in diabetes. The modification characterised by protein glycosylation is associated with diabetes, and glycosylated lipoproteins such as e.g. LDL, IDL, VLDL and HDL can be expected to be functionally abnormal. Accordingly, the accumulation of glycosylated LDL in the plasma of a diabetic subject can be perceived to enhance cholesterol ester accumulation. Also, glycosylation of HDL can be expected to impair the ability of HDL binding to the HDL receptor. This impaired binding is likely to reduce the level of intracellular cholesterol efflux. Accordingly, glycosylated HDL may well be another factor potentially contributing to the accumulation of cholesterol in the arterial cell wall. A composition according to the present invention may be effective in preventing, alleviating, treating, reducing and/or eliminating lipoprotein glycosylation in a diabetic subject. In addition, a composition according to the present invention may also be effective in preventing lipoprotein modification caused e.g. by oxidation, chemical modification such as chemical cross-linking, or modifications caused by an alteration in the lipid composition of the lipoprotein, such as any increase or decrease in the content of triglycerides, cholesterol esters, free cholesterol, and apoiipoproteins.

Glycosylated lipoproteins have been suggested to be the subject of further processing leading to the formation of hyperglycosylated compounds. Glycosylation and hyperglycosylation of proteins including lipoproteins in both plasma and the arterial wall can also be expected to be a risk factor for cardiovascular disease including arteriosclerosis in diabetic subjects. Accordingly, a composition according to the present invention may be capable of preventing, treating, reducing, alleviating and/or eliminating the accumulation of hyperglycosylated proteins in both serum and cells of the arterial wall. By doing so, the composition is acting to decrease the amount of LDL becoming "trapped" in the arterial wall due to the high degree of glycosylation of arterial wall proteins. A composition according to the present invention may also be effective in alleviating and/or preventing any change to the endothelial cell wall that increase LDL "trapping", and it may be effective in restoring the formation of cells with normal permeability and adhesion parameters.

Lipoprotein glycosylation, hyperglycosylation, oxidation and/or auto-oxidative glycosylation, are risk factors for cardiovascular disease such as arteriosclerosis in diabetes. Accordingly, a composition according to the present invention may be effective in eliminating, preventing, alleviating, treating and/or reducing any incidence of lipoprotein glycosylation, hyperglycosylation, oxidation and/or auto-oxidative glycosylation. According to one presently preferred hypothesis, the phytoestrogen compound of a composition according to the present invention is capable of counteracting incidences. The phytoestrogen compound may also be capable of preventing, reducing and/or eliminating the formation of e.g. free radicals that are likely to be involved in such processes, and a composition according to the present invention may be effective in being, promoting, and/or facilitating the formation of an effective antioxidant defence system for counteracting glycosylation, hyperglycosylation, oxidation and/or auto-oxidative glycosylation of serum proteins and proteins including lipoproteins of the arterial cell wall.

Since oxidative stress is a characteristic of diabetes and possibly a contributory factor to among others lipoprotein oxidation and/or glycosylation, and since no efficient antioxidant protection exists due to e.g. significantly decreased levels in diabetic subjects of antioxidants such as e.g. ascorbic acid, a composition according to the present invention may be effectively acting as an antioxidant in preventing lipoprotein oxidation and/or glycosylation.

A composition according to the present invention may be effectively acting as an antioxidant in preventing lipoprotein oxidation and/or glycosylation. By the term auto-oxidative glycosylation, or glycoxidation, is understood a reaction catalysed e.g. by reducing sugars that leads to an oxidative modification and/or cross-linking of proteins. The rate of such a process can be expected to be increased in the presence of high glucose concentrations since the oxidising potential is significantly increased under such circumstances. An increased production of free radicals and lipid peroxidation may also contribute to the formation of auto-oxidative glycosylated lipoproteins and this contribution may also be effectively prevented and/or eliminated by a composition according to the present invention.

According to another presently preferred hypothesis, the binding of a phytoestrogen compound, such as e.g. isoflavones, to a receptor in the arterial wall, such as e.g. the estrogen receptor, or an estrogen-like receptor, is involved in or effective in controlling uptake of cholesterol and/or triglycerides in the arterial wall, possibly by regulating the permeability of said wall and/or the mechanism of cholesterol and/or triglyceride transport across cellular membranes. Consequently, the binding of isoflavones such as e.g. genistein and/or daidzein to a receptor in the arterial wall may prevent cholesterol and/or triglycerides from entering the arterial wall, or reduce and/or substantially eliminate the amount of cholesterol and/or triglycerides that enters the arterial wall. Receptor binding of isoflavones in the arterial wall is particularly effective in controlling, preventing and/or eliminating fatty streak formation and/or fibrous plaque development and/or effective in mediating a regression of one or both of said arteriosclerotic conditions.

Binding of isoflavones such as e.g. genistein and/or daidzein to a receptor in the arterial wall, preferably an estrogen receptor or an estrogen-like receptor, results in an increased nitric oxide synthesis in the endothelial cells of the arterial wall. Nitric oxide is known to exert anti-arteriosclerotic effects including inhibition of platelet adhesion and aggregation, and of smooth muscle cell proliferation.

The establishment of an oxidative potential occurs concomitantly with, and is very likely caused by, a decrease in cellular antioxidant defence systems. This hypothesis is supported by the fact that e.g. ascorbic acid concentrations are decreased in many diabetic individuals. Accordingly, a composition according to the present invention may be effective in acting as an antioxidant. This action reduces and/or eliminates LDL, VLDL, IDL and/or HDL susceptibility to oxidation. Concomitantly with a direct anti-oxidative effect, a composition according to the present invention may also lower the increased serum glucose levels and by doing so, a composition according to the present invention may be effective in reducing the oxidising potential causing and/or contributing to oxidative stress.

Furthermore, a composition according to the present invention may also be effective in reducing an enhanced susceptibility to endothelial injury and/or for alleviating and/or restoring and/or improving an inefficient endothelial cell repair mechanism. One effect of such an action exerted by a composition according to the present invention is to direct macrophage development away from foam cell formation and to increase the potential of generating arterial smooth muscle cells.

The unique dyslipidaemia associated with type 2 diabetes is a major risk factor for cardiovascular disease, and prevention, alleviation, reduction and/or elimination of dyslipidaemia in diabetic subjects is a prime objective of administration of a composition according to the present invention to a diabetic individual. Another important objective of such an administration is the development in a diabetic subject of a gradually reduced insulin resistance and/or a gradually improved glucose tolerance. Since increasing insulin resistance and impaired glucose tolerance are key elements in the progression of type 2 diabetes, the same factors most also be a natural focus of any preventive treatment.

In another presently preferred hypothesis, a composition according to the present invention will promote and/or mediate a reduction in arterial wall thickness and lead to a reduction in the amount of LDL entering the wall. It is believed that an increased thickness of the arterial wall is positively associated with an increased uptake of LDL-particles that are likely to either aggregate or oxidize within the cells of the arterial wall.

Also, a composition according to the present invention may be capable of reducing, eliminating and/or preventing the formation of increased serum levels of lipoprotein (a) in a diabetic subject. Lipoprotein (a) levels may primarily be genetically determined, and no current cardiovascular medications are thought effective in lowering serum levels of lipoprotein (a).

The composition can also be used for protecting men and/or women against arteriosclerosis.

Treatment with the composition according to the present invention can result in keeping the blood vessels free from cholesterol plaques or reducing the level of cholesterol plaques.

The composition according to the present invention can be used for treatment of hypertension and/or cardiovascular diseases.

Cancer

The composition according to the present invention can have curative properties in some type of cancer, apparently through growth inhibition of cancer cells. The composition can e.g. be used in treatment of B-cell precursor (BCP)-leukemia, breast cancer and colorectal cancer.

Other Diseases

The red clover extract according to the present invention can be used for a variety of medicinal purposes, such as the treatment of Alzheimer's disease, dementia, bronchitis, burns, ulcers, sedation, inflammatory diseases and asthma.

The composition according to the present invention can also be used for improving the urination of patients having enlarged prostate.

The composition according to the present invention also have antioxidant effects.

The composition according to the present invention has an anabolic effect leading to increased insulin sensitivity. The composition according to the present invention can increase or induce muscle—e.g. to obtain increase muscle mass. This can e.g. be used for rehabilitation of old people or treatment of people with muscle related diseases or weak muscles.

In another embodiment the invention relates to treatment of depression and/or anxiety e.g. associated with the post-menopausal syndrome.

In one aspect the present invention relates to the following treatments:

A method of treatment of an individual suffering from, or at risk of developing, menopause-related symptoms, such as one or more of hot flashes, perspiration, and headache, said method comprising the steps of administering to said individual the composition according to the present invention, wherein said treatment is prophylactic, ameliorating or curative.

A method of treatment of an individual suffering from, or at risk of developing, premenstrual syndrome, said method comprising the steps of administering to said individual the composition according to according to the present invention, wherein said treatment is prophylactic, ameliorating or curative.

A method of treatment of an individual suffering from, or at risk of developing, osteoporosis, said method comprising the steps of administering to said individual the composition according to according to the present invention, wherein said treatment is prophylactic, ameliorating or curative.

A method of treatment of an individual suffering from, or at risk of developing, arteriosclerosis, said method comprising the steps of administering to said individual the composition according to according to the present invention, wherein said treatment is prophylactic, ameliorating or curative.

A method of treatment of an individual suffering from, or at risk of developing, cholesterol plaques, said method comprising the steps of administering to said individual the composition according to any of according to the present invention, wherein said treatment is prophylactic, ameliorating or curative.

A method of treatment of an individual suffering from, or at risk of developing, hypertension, said method comprising the steps of administering to said individual the composition according to according to the present invention, wherein said treatment is prophylactic, ameliorating or curative.

A method of treatment of an individual suffering from, or at risk of developing, cardiovascular diseases, said method comprising the steps of administering to said individual the composition according to according to the present invention, wherein said treatment is prophylactic, ameliorating or curative.

A method of treatment of an individual suffering from, or at risk of developing, a cancer disease, such as B-cell precursor (BCP)-leukemia, breast cancer, prostate cancer, cervical cancer and colorectal cancer, said method comprising the steps of administering to said individual the composition according to according to the present invention, wherein said treatment is prophylactic, ameliorating or curative.

A method of treatment of an individual suffering from, or at risk of developing one or more skin diseases such as eczema, psoriasis and acne.

A method of treatment of an individual suffering from, or at risk of developing one or more respiratory diseases such as cough, asthma and bronchitis.

A method of treatment of an individual suffering from, or at risk of developing one or more types of emotional distress including mood swings, dysphoria, dysthymia and/or depression. The emotional distress can e.g. be related to menopause and/or PMS.

Dosage

In one embodiment the daily dose of lactic acid fermented isoflavones derived from red clover suitable for e.g. a human being is from 5 to 150 mg/day of isoflavones (defined as the total amount of Daidzein, Genistein, Formononetin, Ononin, Biochanin A and Sissotrin or as the total amount of Genistein, Formononetin, Biochanin A, Malonyl-glucoside daidzein, Malonyl-glucoside glycitein, Malonyl-glucoside genistein, Acetyl-glucoside daidzein, and glycitein), such as from 2 mg/day to 4 mg/day, for example from 4 mg/day to 6 mg/day, such as from 6 mg/day to 8 mg/day, for example from 8 mg/day to 10 mg/day, such as from 10 mg/day to 12 mg/day, for example from 12 mg/day to 14 mg/day, such as from 14 mg/day to 16 mg/day, for example from 16 mg/day to 18 mg/day, such as from 18 mg/day to 20 mg/day, for example from 20 mg/day to 22 mg/day, such as from 22 mg/day to 24 mg/day, for example from 24 mg/day to 26 mg/day, such as from 26 mg/day to 28 mg/day, for example from 28 mg/day to 30 mg/day, such as from 30 mg/day to 32 mg/day, for example from 32 mg/day to 34 mg/day, such as from 34 mg/day to 36 mg/day, for example from 36 mg/day to 38 mg/day, such as from 38 mg/day to 40 mg/day, for example from 40 mg/day to 45 mg/day, such as from 45 mg/day to 50 mg/day, for example from 50 mg/day to 60 mg/day, such as from 60 mg/day to 70 mg/day, for example from 70 mg/day to 80 mg/day, such as from 80 mg/day to 90 mg/day, for example from 90 mg/day to 100 mg/day, such as from 100 mg/day to 125 mg/day, for example from 125 mg/day to 150 mg/day, or any combination of these intervals.

In one embodiment the daily dose of lactic acid fermented Daidzein derived from red clover is from 0.05% to 10% of the daily dose of isoflavones (defined as the total amount of Daidzein, Genistein, Formononetin, Ononin, Biochanin A and Sissotrin), such as from 0.05% to 0.1%, for example from 0.1% to 0.5%, such as from 0.5% to 1%, for example from 1% to 1.5%, such as from 1.5% to 2%, for example from 2% to 2.5%, such as from 2.5% to 3%, for example from 3% to 3.5%, such as from 3.5% to 4%, for example from 4% to 4.5%, such as from 4.5% to 5%, for example from 5% to 5.5%, such as from 5.5% to 6%, for example from 6% to 7%, such as from 7% to 8%, for example from 8% to 9%, such as from 9% to 10%, for example from 10% to 11%, such as from 11% to 12%, for example from 12% to 13%, such as from 13% to 14%, for example from 14% to 15%, or more than 15% or any combination of these intervals.

In one embodiment the daily dose of lactic acid fermented Genistein derived from red clover is from 0.05% to 10% of the daily dose of isoflavones (defined as the total amount of Daidzein, Genistein, Formononetin, Ononin, Biochanin A and Sissotrin), such as from 0.05% to 0.1%, for example from 0.1% to 0.5%, such as from 0.5% to 1%, for example from 1% to 1.5%, such as from 1.5% to 2%, for example from 2% to 2.5%, such as from 2.5% to 3%, for example from 3% to 3.5%, such as from 3.5% to 4%, for example from 4% to 4.5%, such as from 4.5% to 5%, for example from 5% to 5.5%, such as from 5.5% to 6%, for example from 6% to 7%, such as from 7% to 8%, for example from 8% to 9%, such as from 9% to 10%, for example from 10% to 11%, such as from 11% to 12%, for example from 12% to 13%, such as from 13% to 14%, for example from 14% to 15%, or more than 15% or any combination of these intervals.

In one embodiment the daily dose of lactic acid fermented Ononin derived from red clover is from 0.05% to 10% of the daily dose of isoflavones (defined as the total amount of Daidzein, Genistein, Formononetin, Ononin, Biochanin A and Sissotrin), such as from 0.05% to 0.1%, for example from 0.1% to 0.5%, such as from 0.5% to 1%, for example from 1% to 1.5%, such as from 1.5% to 2%, for example from 2% to 2.5%, such as from 2.5% to 3%, for example from 3% to 3.5%, such as from 3.5% to 4%, for example from 4% to 4.5%, such as from 4.5% to 5%, for example from 5% to 5.5%, such as from 5.5% to 6%, for example from 6% to 7%, such as from 7% to 8%, for example from 8% to 9%, such as from 9% to 10%, for example from 10% to 11%, such as from 11% to 12%, for example from 12% to 13%, such as from 13% to 14%, for example from 14% to 15%, or more than 15% or any combination of these intervals.

In one embodiment the daily dose of lactic acid fermented Sissotrin derived from red clover is from 0.05% to 10% of the daily dose of isoflavones (defined as the total amount of Daidzein, Genistein, Formononetin, Ononin, Biochanin A and Sissotrin), such as from 0.05% to 0.1%, for example from 0.1% to 0.5%, such as from 0.5% to 1%, for example from 1% to 1.5%, such as from 1.5% to 2%, for example from 2% to 2.5%, such as from 2.5% to 3%, for example from 3% to 3.5%, such as from 3.5% to 4%, for example from 4% to 4.5%, such as from 4.5% to 5%, for example from 5% to 5.5%, such as from 5.5% to 6%, for example from 6% to 7%, such as from 7% to 8%, for example from 8% to 9%, such as from 9% to 10%, for example from 10% to 11%, such as from 11% to 12%, for example from 12% to 13%, such as from 13% to 14%, for example from 14% to 15%, or more than 15% or any combination of these intervals.

In one embodiment the daily dose of lactic acid fermented Formononetin derived from red clover is from 30% to 80% of the daily dose of isoflavones (defined as the total amount of Daidzein, Genistein, Formononetin, Ononin, Biochanin A and Sissotrin), such as from 30% to 35%, for example from 35% to 40%, such as from 40% to 45%, for example from 45% to 50%, such as from 50% to 55%, for example from 55% to 60%, such as from 60% to 65%, for example from 65% to 70%, such as from 70% to 75%, for example from 75% to 80%, or more than 80% or any combinations of these intervals.

In one embodiment the daily dose of lactic acid fermented Biochanin A derived from red clover is from 15% to 50% of the daily dose of isoflavones (defined as the total amount of Daidzein, Genistein, Formononetin, Ononin, Biochanin A and Sissotrin), such as from 15% to 20%, for example from 20% to 25%, such as from 25% to 30%, for example from 30% to 35%, such as from 35% to 40%, for example from 40% to 45%, such as from 45% to 50%, or more than 50% or any combinations of these intervals.

In one embodiment of the invention the administration of the composition according to the present invention must result in a blood concentration of total isoflavone of from 1-10 micromoles/liter to achieve the desired effect. In another embodiment the administration of the composition according to the present invention must result in a blood concentration of total isoflavone of from 0.1-100 micromoles/liter to achieve the desired effect such as from 0.1 micromoles/liter to 0.5 micromoles/liter, for example from 0.5 micromoles/liter to 1 micromoles/liter, such as from 1 micromoles/liter to 2 micromoles/liter, for example from 2 micromoles/liter to 3 micromoles/liter, such as from 3 micromoles/liter to 4 micromoles/liter, for example from 4 micromoles/liter to 5 micromoles/liter, such as from 5 micromoles/liter to 6 micromoles/liter, for example from 6 micromoles/liter to 7 micromoles/liter, such as from 7 micromoles/liter to 8 micromoles/liter, for example from 8 micromoles/liter to 9 micromoles/liter, such as from 9 micromoles/liter to 10 micromoles/liter, for example from 10 micromoles/liter to 15 micromoles/liter, such as from 15 micromoles/liter to 20 micromoles/liter, for example from 20 micromoles/liter to 25 micromoles/liter, such as from 25 micromoles/liter to 30 micromoles/liter, for example from 30 micromoles/liter to 35 micromoles/liter, such as from 35 micromoles/liter to 40 micromoles/liter, for example from 40 micromoles/liter to 45 micromoles/liter, such as from 45 micromoles/liter to 50 micromoles/liter, for example from 50 micromoles/liter to 60 micromoles/liter, such as from 60 micromoles/liter to 70 micromoles/liter, for example from 70 micromoles/liter to 80 micromoles/liter, such as from 80 micromoles/liter to 90 micromoles/liter, for example from 90 micromoles/liter to 100 micromoles/liter, or any combinations of these intervals.

Oral supplements may comprise between 50 mg and 100 mg of isoflavone. In another embodiment the oral supplements comprises between 1 mg and 500 mg of isoflavone such as for example from 1 mg to 5 mg, such as from 5 mg to 10 mg, for example from 10 mg to 20 mg, such as from 20 mg to 30 mg, for example from 30 mg to 40 mg, such as from 40 mg to 50 mg, for example from 50 mg to 60 mg, such as from 60 mg to 70 mg, for example from 70 mg to 80 mg, such as from 80 mg to 90 mg, for example from 90 mg to 100 mg, such as from 100 mg to 150 mg, for example from 150 mg to 200 mg, such as from 200 mg to 250 mg, for example from 250 mg to 300 mg, such as from 300 mg to 350 mg, for example from 350 mg to 400 mg, such as from 400 mg to 450 mg, for example from 450 mg to 500 mg, or any combination of these intervals.

The period of treatment is preferably in the range of from 1 to 12 months or more, such as from 2 weeks to 9 months, for example from 3 weeks to 6 months, such as from 4 weeks to 4 months, such as from 6 weeks to 3 months. However, the period of treatment shall not be limited to these periods and may e.g. be longer than 12 months, such as e.g. a lifelong treatment in order to prevent and/or alleviate the disease such as type 2 diabetes and/or a cardiovascular disease in connection therewith.

EXAMPLES

Example 1: Production of Red Clover Extract

Red clovers are harvested and added to a container.
The red clovers are heated to 70° C. for 1 hour.

The liquid from the red clovers—i.e. the red clover extract—is extracted from the red clovers by compression of the red clovers. The red clover extract is transferred to a separate container and kept at 3-5° C.

Lactic acid bacteria are added to the red clover extract.

The red clover extract will be allowed to be fermented for 6 months. During this period the red clover extract is transferred to a new container every 6 to 8 weeks. The fermentation is performed at 3-5° C.

The pH of the red clover extract will decrease to about 4 or less than 4 during the fermentation process. The decrease of the pH results in conservation of the red clover extract.

The red clover extract will subsequently be stable for 1.5 to 2 years.

Analysis of Isoflavone Content in the Red Clover Extract

Table 1 herein below indicated the content of different isoflavones in the red clover extract. The samples have been diluted in methanol and analysed by HPLC with UV and MS detection.

TABLE 1

| | isoflavone content in Red Clover Extract | | | | | |
|---|---|---|---|---|---|---|
| | | Red clover | | | | |
| | | 12-1 | 12-2 | 12-3 | 12-4 | 12-5 |
| | | | | DB Lab no. | | |
| Parameter | | 17396.01 mg/kg | 17396.02 mg/kg | 17396.03 mg/kg | 17396.04 mg/kg | 17396.05 mg/kg |
| Daidzein | Aglycone | 2.2 | 1.1 | 2.1 | 4.5 | 5 |
| Genistein | Aglycone | 5.8 | 2.9 | 7.0 | 6.5 | 5.5 |
| Formononetin | Biochanin B | 143 | 107 | 140 | 140 | 131 |
| Ononin | Ononin is the 7-O-glucoside of formononetin | 9.1 | 9.9 | 19.5 | 14.2 | 4.7 |
| Biochanin A | | 82.1 | 57.3 | 78.2 | 72.6 | 63.3 |
| Sissotrin | Biochanin A 7-O-β-D-glucopyranoside | 9.0 | 8.6 | 13.1 | 7.6 | 1.1 |
| Sum | | 251.2 | 186.8 | 259.9 | 245.4 | 210.6 |
| | | % | % | % | % | % |
| Drymatter content | | 3.54 | 3.75 | 4.15 | 4.32 | 4.23 |

Example 2: Clinical Data

Objective

The aim of this study was to determine whether a three month daily intake of the Red Clover preparation according to the present invention can alleviate hot flush symptoms and associated disorders when compared with placebo.

The specific objectives of the study comprise:

1) To examine the extent to which Red Clover extract can reduce incidence and intensity of vasomotor symptoms.

2) To examine whether daily Red Clover extract supplementation can reduce bone mineral resorption and help maintain BMD (Bone Mineral Density) in the short term.

3) To assess the effect of Red Clover extract at promoting cardiovascular health, inducing positive lipid profile and reducing inflammatory status.

Method

Summary of Method 60 menopausal women were randomly assigned a three month daily Red Clover preparation (with 37.1 mg isoflavones per day) or equivalent placebo. The progressions of the menopause symptomology were evaluated with a variety of methods. Menopausal symptoms were recorded using objective 24 hour skin conductance and the Green Menopause index questionnaire. Bone status (bone mineral density and bone mineral content) was assessed using dual X ray absorptiometry at the femoral neck and lumbar spine. Blood tests were taken to verify lipid status (low density lipoprotein, high density lipoprotein, total cholesterol and triglycerides) of participants, as well as inflammatory biomarkers (IL-2, IL-4, IL-5, IL-6, IL-10, IL-12, IL-13 and IFN-γ) and C-reactive protein. 24 hour ambulatory blood pressure was measured to assess cardiovascular status over the duration of the trial.

Participant Recruitment

Participants were recruited either through the hospital, by practising doctors within the local area or through advertisements in local newspapers and flyers.

60 menopausal women were randomly assigned a three month daily Red Clover preparation (with 37.1 mg isoflavones per day) or equivalent placebo.

The means and standard error of baseline characteristics (age, BMI (Body Mass Index), FSH (Follicle Stimulating Hormone), hysterectomy and smoker) for participants that fully completed all 3 months of the study are specified in table 2 herein below. There were no significant differences between baseline characteristics.

TABLE 2

The baseline characteristics for placebo (blue) and treatment group (red). P values represent non-significant differences ($P > 0.05$) between subject groups prior to week 0.

| | Treatment | Placebo | Unpaired T Test (P sig. <0.05) |
|---|---|---|---|
| Age (mean) | 52.28 | 52.25 | |
| SEM | (3.55) | (2.28) | NS (P = 0.6787) |
| BMI (mean) | 26.19 | 25.50 | |
| SEM | (5.11) | (3.23) | NS (P = 0.6871) |
| FSH (mean, IU/l) | 72.06 | 71.89 | |
| SEM | (25.68) | (26.11) | NS (P = 0.8873) |
| Hysterectomy (mean) | 0.09 | 0.11 | |
| SEM | (0.29) | (0.31) | NS (P = 0.8659) |

TABLE 2-continued

The baseline characteristics for placebo (blue) and treatment group (red). P values represent non-significant differences (P >0.05) between subject groups prior to week 0.

|  | Treatment | Placebo | Unpaired T Test (P sig. <0.05) |
|---|---|---|---|
| Smoker (mean) | 0.09 | 0.21 |  |
| SEM | (0.29) | (0.41) | NS (P = 0.1984) |

Inclusion Criteria
    Acknowledged problems with menopausal symptoms (>5 hot flushes per day)
    40-65 years of age
    BMI 18-35
    Have a reported variable cycle length of >7 days different from normal
    FSH level ≥35 Ul/L Exclusion Criteria
    Had participated in any other clinical studies in the last 3 months
    A history of cancer, cardiovascular, psychiatric, neurological, nephritic or renal disorders
    History of drug or alcohol abuse
    Severe cardiovascular, psychiatric, neurological, and/or kidney disease.
    Used hormonal contraceptives within the least 3 months
    Blood pressure diastolic ≥160 or systolic ≤60
    Reported excessive dietary intake of isoflavone rich foods
    Pregnant and lactating women
    Failure to agree with and/or comply with the guidelines set out prior to project start and over the course of the study period.

Study Design

The study was set up as a 3 month, double blind, parallel designed, randomised control trial. The participants were menopausal women suffering and/or expressing symptoms characteristic of the menopause. They were screened and randomised into either placebo or active treatment groups. The screening and all phases of the study took place at Syghus Vendsyssel, Center for Klinisk Forskning, Bispensgade 37, 9800 Hjørring, Denmark (Hospital Vendsyssel, Centre for Clinical Research).

After randomisation, participants in each group received a daily dosage of 150 ml extract or the equivalent dose of placebo (2×75 ml/d), equating to an approximate total of 13.5 litres over 90 days. At each meeting period every participant was given either Red Clover extract or placebo as required, approximating to 2-4 litres per visit as necessary (accounting for losses). Empty 2 litre containers were collected and noted down for each participant as a measure for compliance to ensure that all participants drank a minimum of 7 over the course of the study.

Participants and the research group met every third week to complete actions specified in FIG. 1. The day prior to week 0 and 12 phases participants were asked to refrain from eating anything from 23:00-8:00 the next day (apart from water) in order to validate blood tests. The participants arriving fasted (for a minimum of 8 hours) were immediately required to provide urine and blood samples (for lipid and inflammation testing), after which they were offered breakfast. Blood sampling was performed by bio-analysts at the Department of Clinical Biochemistry, Bispensgade 37 9800 Hjørring, Denmark; supervised by a qualified bio-analyst. A total of four 5 ml EDTA anti coagulated plasma samples were taken both at week 0 and 12 per participant. During sampling, blood tests were separated into bio bank, compliance, lipids and inflammatory marker groups. Both blood and urine samples were then frozen for storage at −80° C. for ~1-4 months and later transported (frozen with dry ice) to the Department of Medicine and Endocrinology MEA, Aarhus University Hospital, Tage-Hansens Gade 2 DK-8000, Denmark and kept at −80° C. until analysis. Participants were required to be scanned by the orthopaedic department using Dual X ray absorptiometry (DXA) at weeks 0 and 12. This took place at the Medicinsk Ambulatorium (The Medical Infirmary), Hjørring; under the supervision of relevant hospital personnel.

24 hour skin conductance and blood pressure (BP) measurements were taken on consecutive days (SC on day one and BP on day two). SC was carried out at weeks 0, 6 and 12, whereas the 24 hour ambulatory BP measurements were only taken during weeks 0 and 12. Participants were informed on how to use each device prior to each test stage. Moreover during these visits (0, 6 and 12) the Green menopause index questionnaire was either directly distributed to participants or, if unable to be complete, sent out as a letter with a return envelope.

Materials and Methods

The Red Clover extract was produced and provided by Herrensmark® v/Michael Mohr Jensen, Assensvej 17, 5580 Nr. Aby, Denmark. Red Clover crops were harvested ~6-8 months before use. Post-harvest processing requires that the plant material be transported to rust free drums. Following this, the red clover mass is pressed and the resulting extract is pumped into large tanks where it is stored at 3-5° C. Aqueous extracts are left within the tanks to undergo lactic acid fermentation for 6 months. During storage, the fermenting extract is routinely moved to a new tank every 6-8 weeks, allowing the pH to gradually fall. By the end of the process the pH of the extract resides at ~4 which preserves the extract. This novel fermentation process is integral for the hydrolysis of isoflavone glycoside and glucoside compounds, which further improves the bioavailability of the plant derived phytoestrogens.

The post-fermentation isoflavone composition and quantification analysis of the final extract was performed by DB lab (DB Lab A/S, Lille Tornbjerg Vej 24, DK-5220 Odense SØ, Denmark). Quantification of compounds was assessed using high performance liquid chromatography with ultra-violet and mass spectrometry detection. A Summit@ LC/MS system consisting of a quaternary pump (P680 LPG), autosampler (ASI 100T), column oven (TCC-100) UV detector (PDA-100) and MS detector (Surveyor MSD Plus), all from Dionex, was used to perform the analysis. Standards for four of the primary isoflavones (genistein, daidzein, formononetin and Biochanin A) and the latter two glycoside derivatives (Ononin and Sissotrin) were obtained from Sigma Aldrich Denmark A/S (Kirkebjerg Allé 84, 2. Sal 2605 Brødby) and sent to DB lab for analysis two months prior to participant screening. The sample (Red Clover extract) was diluted 10 times (50 ml to 5 ml) by methanol and analysed, quantification by UV detection was used when possible and if necessary by MS if peak heights were too small or contaminated by other components.

The results of the analysis—shown in Table 3 herein below—revealed that the majority of the isoflavones were as aglycones, although total conversion was not achieved (verified by the presence of ononin and sissotrin glucosides). In accordance with the DB lab analysis the participants who received active treatment were given a dose of 37.1 mg/d (of which 33.78 mg/d were aglycones). Due to financial constraints 6 of the other sugar bound isoflavone forms, as well as glycitein and glycitin were not included within the analysis. Meaning that total isoflavone content of this preparation is not comparable with other studies, i.e. the actual dosage in these terms would be higher than 37.1 mg/d.

TABLE 3

Red Clover Extract Isoflavone content

| Isoflavone | Concentration |
| --- | --- |
| Daidzein | 7.9 mg/litre |
| Genistein | 20.9 mg/litre |
| Biochanin A | 45.1 mg/litre |
| Formononetin | 95.0 mg/litre |
| Ononin | 9.0 mg/litre |
| Sissotrin | 7.6 mg/litre |
| Dry matter content | 30.4 g/litre |

Placebo and Red Clover Formulations

Due to the bitter/sour tasting qualities of the RC extract, further manipulation of the flavour characteristics was achieved by the addition of stevia and a natural sugar free raspberry/orange flavouring. Specifically, 90 litres of either water (placebo) or Red Clover extract were sweetened with 18 g stevia and 6.3 litres of sugar free raspberry/orange flavouring to mask differences in taste. The placebo was a water-based formulation in which 90 litres of water was mixed with 250 g kavli brun kulør (brown food colouring) to achieve likeness in appearance to RC extract.

High Sensitivity C Reactive Protein Assay

The principle of High sensitivity C-reactive protein assay (hs-CRP) is outlined by Rifai et al (N. Rifai, R. P. Tracy, and P. M. Ridker, "Clinical efficacy of an automated high-sensitivity C-reactive protein assay.," *Clinical chemistry*, vol. 45, no. 12, pp. 2136-41, December 1999.). In short it employs the use of specific monoclonal antibodies that are targeted against an antigenic factor on the C reactive protein molecule. Antibodies from the mice act as an immobiliser, in solid phase testing, enabling specimen C reactive protein to bind to the anti-CRP antibodies on the microtiter wells. A goat anti-CRP linked antibody-enzyme (horseradish peroxidase) in a conjugate solution is than applied in order to sandwich CRP molecules between itself and the solid phase simultaneously. Post 45 minute incubation, at room temperature, the plate wells are washed with water thereby removing any unbound labelled antibodies. Addition of Tetramethylbenzidine (TMB) reagent, given an incubation time of 20 minutes, creates a blue colour; this colour development is then stopped by addition of 1N HCL transforming the colour from blue to yellow. Thereafter the concentration of CRP is directly proportional to the intensity of the colour of the test sample, which is measured spectrophotometrically at 450 nm.

In this study 120 plasma samples kept at −80° C., stored at −20° C. (the day prior to analysis) and then thawed for use. All specimens, controls and standards were analysed in duplicate, using hs-CRP ELISA kits (DRG Instrument GmbH, Marburg, Germany) and according to the manufacturers' instructions.

In brief, 10 µl of CRP samples, controls and standards were dispensed into corresponding wells. Thereafter 100 µl of CRP enzyme conjugate reagent was added to each well and then mixed extensively for 30 seconds. Wells were then allowed to incubate for 45 minutes at room temperature. Incubation mixture was then removed by rinsing (with deionised water) and flicking plate contents into a waste container five times. The ELISA plate was then stuck over paper towels to ensure removal of excess water. 100 µl of TMB solution was added to each well and incubated for 20 minutes, there after 100 µl of stop solution was introduced to each well. After 30 seconds of gently mixing the colour of controls and specimens had shifted from blue to yellow and within 15 minutes absorbance of each well was read at 450 nm using a well reader.

Bio-Rad Multiplex Assay for Inflammatory Markers

The Bio-Plex cytokine assay system employs Luminex multianalyte profiling technology that enables for separate and multiplex analysis of approximately 100 different colour coded polystyrene bead (5.6 µm) set analytes in a single microplate well (D. A. A. Vignali, "Multiplexed particle-based flow cytometric assays," *Journal of Immunological Methods*, vol. 243, no. 1-2, pp. 243-255, September 2000). Fluorescently dyed microspheres coupled with biomolecules targeted to a specific cytokine are bound together in solution, resulting biochemical reactions are then detected using a dual laser flow cytometer. The flow cytometer together with other optics enable for accurate measurement of reactions occurring on the surface of the beads. The florescent output from these reactions is effectively managed at high speed using digital signal processor. Washing phases are used to remove unbound beads during testing and biotinylated detection antibodies specific to different epitope on the cytokine is added, thereby enabling antibodies to fully engulf the target cytokine. Streptavidin-phycoerythrin is then used to bind to biotinylated antibodies, which then are taken up by the flow-based Bio-Plex suspension array system. This system is used to quantify and identify individual reactions based fluorescence and bead colour data. Reaction magnitude is monitored by reporter molecules (that are fluorescently labelled) that associate with each target protein.

The multiplex cytokine kit (Bio-Rad, Hercules, Calif., USA) analysed the following listed cytokines: IL-2, IL-4, IL-5, IL-6, IL-10, IL-12, IL-13 and IFN-γ. Analyses were carried out using a similar approach to de Jager et al (W. de Jager, H. te Velthuis, B. J. Prakken, W. Kuis, and G. T. Rijkers, "Simultaneous Detection of 15 Human Cytokines in a Single Sample of Stimulated Peripheral Blood Mononuclear Cells," *Clinical and Vaccine Immunology*, vol. 10, no. 1, pp. 133-139, January 2003).

To summarise, the 50 µl of frozen blood plasma (inflammation labelled) and standards for cytokines were diluted in plasma dilution buffer and then added plate wells. Thereafter, samples and 50 µl of antibody-coupled micro bead sets (2000/spheres per well) were incubated together and left for 30 minutes (in darkness and at room temperature) on a plate shaker running at 300 rpm. During this phase they were filter washed with 100 µl of wash buffer in triplicate. Secondary detection antibody dilution (25 ml/well) was then added to each well and incubated on a plate shaker (300 rpm) for 30 min, again at room temperature and filter washed in triplicate using 100 µl of wash buffer. 50 µl of streptavidin-phycoerythrin (16 µg/ml in assay buffer) was introduced to the wells, after which incubation under the same conditions continued for the first 10 min on a plate shaker. Using the vacuum manifold, the unbound analytes were filtered through the wells and the beads were washed for a final time with 100 µl of wash buffer. Afterwards, addition of 125 µl of assay buffer was put in each well and the plate was set for 1 minute on the plate shaker (500 rpm) and then for a further 3 minutes at the original 300 rpm. 50 µl of sample was examined on the Bio-Plex system and all data from samples were analysed using Bio-Plex Manager system. Detection utilising multiplex bead technology is shown to have a high degrees of precision, with documented inter assay variations of 10-20% and intra-assay ranges <10% in variation (W. de Jager, H. te Velthuis, B. J. Prakken, W. Kuis, and G. T. Rijkers, "Simultaneous Detection of 15 Human Cytokines in a Single Sample of Stimulated Peripheral Blood Mononuclear Cells," *Clinical and Vaccine Immunology*, vol. 10, no. 1, pp. 133-139, January 2003; and A. Bruneel, M. Dehoux, A. Barnier, and A. Boutten, "External evaluation of the dimension vista 1500® intelligent lab system.," *Journal of clinical laboratory analysis*, vol. 26, no. 5, pp. 384-97, September 2012).

Analysis of Blood Lipids

Blood plasma lipids were analysed using Dimension Vista analyser (Dade Behring, Newark, Nebr.) that combines four technologies (i.e. photometry, nephelometry, V-LYTE integrated multisensory potentiometry, and LOCI chemiluminescence) (A. Bruneel, M. Dehoux, A. Barnier, and A. Boutten, "External evaluation of the dimension vista 1500® intelligent lab system.," *Journal of clinical laboratory analysis*, vol. 26, no. 5, pp. 384-97, September 2012). Total cholesterol (TC), high-density lipoprotein cholesterol (HDL-C) and triglyceride (TG) concentrations were measured on using immunonephelometry assay. Final LDLC levels were calculated using the Friedewald equation, i.e. LDLC=TC minus HDLC minus very-low-density lipoprotein cholesterol (estimated as triglycerides divided by 5) [G. R. Warnick, R. H. Knopp, V. Fitzpatrick, and L. Branson, "Estimating low-density lipoprotein cholesterol by the Friedewald equation is adequate for classifying patients on the basis of nationally recommended cutpoints.," *Clinical chemistry*, vol. 36, no. 1, pp. 15-9, January 1990]. Overall of 120 blood tests in the form of plasma were kept at −80° C., (department of Clinical Biochemistry, Bispensgade 37 9800 Hjørring) the day prior to analysis, then thawed and kept on ice during use.

Triglycerides were measured using an enzymatic procedure, where plasma aliquots were incubated with lipoprotein lipase-enzyme reagent that converts TG to free glycerol and fatty acids. In this reaction, glycerolkinase catalyses the phosphorylation of glycerol with ATP to glycerol-3-phosphate, then glycerol-3-phosphate oxidase (GPO) is used to oxidise glycerol-3-phosphate to dihydroxyacetone phosphate and $H_2O_2$. This catalytic peroxidation forms quinoneimine from $H_2O_2$ along with aminoantipyrine and 4-chlorophenol. The variation in absorbance, due to the formation of quinoneimine is directly proportional to the total concentration of glycerol and its precursor concentrations in the sample, which are measured using a bi-chromatic (510 nm and 700 nm) endpoint technique.

Plasma TC concentrations were assessed using enzymatic method described by Allain et al (1974) (C. C. Allain, L. S. Poon, C. S. Chan, W. Richmond, and P. C. Fu, "Enzymatic determination of total serum cholesterol.," *Clinical chemistry*, vol. 20, no. 4, pp. 470-5, April 1974). In summary, cholesterol esterase is used to catalyze cholesterol ester haemolyse within the plasma samples to generated free cholesterol. Newly converted free cholesterol together with the preexisting cholesterol is oxidized in one reaction, mediated by the addition of cholesterol oxidase, which forms cholest-4-en-3-one and $H_2O_2$. Addition of horseradish peroxidase utilizes $H_2O_2$ to oxidise N,N diethylanilin-HCl/4-aminoantipyrin (DEA-HCl/AAP) creating a chromophore that can be absorbed at 540 nm. Absorption of the oxidised DEA-HCL/APP is directly proportional with the concentration of TC and is measured with a polychromatic (540, 452, 700 nm) end point technique.

HDL-C assay can directly quantify plasma HDL-C levels directly without the requirement for pre-treatment or specialised centrifugation steps by using two reagents. The initial reaction generates water soluble complexes of VLDL, chylomicrons and LDL through the addition of dextran and magnesium sulphate. These complexes are resistant to polyethylene glycol-modified cholesterol esterase (PEG-CE) and polyethylene glycol cholesterol oxidase (PEG-CO) that is applied to react specifically with HDL cholesterol. The second reaction, in the presence of oxygen, HDL-C is oxidised to $\Delta$-4-cholestenone and $H_2O_2$. $H_2O_2$ then reacts with N (2-hydroxy-3-sulfopropyl) 3,5-dimethoxyaniline and 4-aminoantipyrine, under exposure to peroxidase to form a coloured dye. This dye is measured using a bi-chromatic technique (at 600 and 700 nm). The intensity of the dye is directly proportional to sample HDL-C concentration.

Dual-Energy X-Ray Absorptiometry

Dual-energy X-ray absorptiometry utilises two x ray beams with differing energy levels that can be used to determine the density of various tissues. It is the photo absorption of these two x rays that enable the DXA to determine both BMD and bone mineral content of an individual at the whole body level or at specific sites, such as the femoral neck, lumbar spine and wards triangle.

Bone mineral density of all participants was assessed by DXA at baseline (week 0) and after 3 months (week 12) using the XR 800 DXA scanner (Norland cooper, surgical, USA, illuminatus software version 4.2.4). The tests were performed under the supervision and guidance of a healthcare professional, participants were asked to remove their clothing and were scanned for 15-20 minutes. During this period, measurements of both the bone mineral content in grams (BMC) and BMD ($g/cm^2$) at the lumbar spine region (L2-L4) and at the femoral neck were taken.

Skin Conductance

Ambulatory 24 hour measurements participants of skin conductance (SC) were taken at weeks 0, 6 and 12. SC was measured using the Q sensor from Affectiva™ that enables measurements of electrodermal activity outside the laboratory (R. W. Picard, "Future affective technology for autism and emotion communication.," *Philosophical transactions of the Royal Society of London. Series B, Biological sciences*, vol. 364, no. 1535, pp. 3575-84, December 2009). The Affectiva Q sensor is applied to the wrist (in a similar fashion to a watch) allowing integrated dual electrodes contact with the ventral side of the arm. The Electrodes measure sweat secretion (SC) of the participant in micro Siemans.

Upon application, the sensor automatically detects skin contact and the unit initiates the measurement phase. The unit continually measures SC, body temperature and the acceleration of the participant, at a sampling rate of 4 Hz (4/min), over a 24 hour period. Throughout the test period all participants were informed to avoid all strenuous physical activity that could affect their sweat secretion and prior to testing consent to adhere to guidelines was given. Furthermore, all participants were briefed on the principals of the sensor and given an instruction manual on its correct usage.

Post-24 hour measurement, all data was collect and saved one research laptop via a USB cable. The data was the stored and coded for each participant, then further arranged by the time and date of the test. Verification of data quality and duration was carried out using Q Software™ any data falling short of 24 hours, plagued with artefacts of physical activity (such as a saw tooth shape or elevated baseline sweat secretion) or segmented more than once, was repeated (J. S. Carpenter, M. A. Andrykowski, R. R. Freedman, and R. Munn, "Feasibility and psychometrics of an ambulatory hot flash monitoring device.," *Menopause (New York, N.Y.)*, vol. 6, no. 3, pp. 209-15, January 1999).

Hot Flush Analysis

Sharp increases in SC coupled with a gradual decline or "swishy tail" are a common and well documented feature of HFs [J. S. Carpenter, M. A. Andrykowski, R. R. Freedman, and R. Munn, "Feasibility and psychometrics of an ambulatory hot flash monitoring device.," Menopause (New York, N.Y.), vol. 6, no. 3, pp. 209-15, January 1999]. There have been many attempts to standardise these or to create a universal measure to fit these assess these. Conventional criteria for a HF event is a ≥2 µmho rise in SC over a 30 second timeframe [R. R. Freedman, "Laboratory and Ambulatory Monitoring of Menopausal Hot Flashes," *Psychophysiology*, vol. 26, no. 5, pp. 573-579, September 1989]. This criterion however, has been shown to be inadequate for many reasons. The performance and sensitivity of this criteria is known to be poor in overweight and obese women, it cannot accommodate for the high inter-individual variability of HFs associated SC increases and it fails to account for the particular shape of each hot flush event increasing the tendency for false positive data [R. C. Thurston, J. A. Blumenthal, M. A. Babyak, and A. Sherwood, "Emotional antecedents of hot flashes during daily life.," *Psychosomatic medicine*, vol. 67, no. 1, pp. 137-46; and L. J. Hanisch, S. C. Palmer, A. Donahue, and J. C. Coyne, "Validation of sternal skin conductance for detection of hot flashes in prostate cancer survivors.," *Psychophysiology*, vol. 44, no. 2, pp. 189-93, March 2007.].

This study used manual interpretation of hot flushes of the 22 hour datasets that included total duration of a HF without the use of cut offs. HF frequency over 24 hours and hot flush intensity of all participants was assessed using Matlab. A bespoke Matlab (named menopauseGUI) program was coded by Esben SøvsøSzocska Hansen (FIG. 2). All datasets of SC were standardised to 22 hours and imported into Matlab. The program enables selection of the start and end point of individual HFs from a single SC measurement. A total of 180 data files were individually evaluated and then saved in an excel format for further statistical interpretation. HF intensity (HFi) was calculated as cumulative area under the curve from each HF where the start point is denoted as A and the end point is B. Post data collection HFi figures were further multiplied by a seasonal variation factor. This factor corresponded to the various individual start-end increases in baseline sweat secretion of participants as a consequence of the rise in ambient temperature in Denmark from March to July of 2012.

Green Menopause Index

A modified version of the Green Menopause index was translated into Danish and participants were required to fill out questionnaires at week 0 on site and under the guidance of a researcher. Subsequent questionnaires (week 6 and 12) were either completed simultaneously with other tests or sent to the home address of a participant with a return envelope. All 21 items from each completed questionnaire were separated into vasomotor, somatic, psychological and sexual groupings and later put into excel for further statistical analysis. For the purposes of this study both depression and anxiety characteristics were not included.

24 Hour Ambulatory Blood Pressure

Blood pressure measurements' were recorded at weeks 0, 6 and 12. The SpaceLab monitor (SpaceLabs Medical, Redmond, Wash.) is a programmable blood pressure monitor that can be worn on the arm (above the elbow) for a 24 hour period. It measures mean arterial blood pressure, heart rate, along with systolic and diastolic blood pressure at intervals determined by a researcher (M. Sun, J. Tien, R. Jones, and R. Ward, "A new approach to reproducibility assessment: clinical evaluation of SpaceLabs Medical oscillometric blood pressure monitor.," *Biomedical instrumentation & technology/Association for the Advancement of Medical Instrumentation*, vol. 30, no. 5, pp. 439-48).

Time interval of measurements, for the duration of the 24 hours, was set to occur once every hour for the day period (6:00-22:00) and once every two hours during the night period (22:00-6:00). Participants were orally briefed and given an instructions manual on proper use of the monitor and cuff. As with the SC testing, participants were required to abstain from medium and heavy exercise for the duration of 24 hour testing. They were also required to note down when they woke up and went to sleep and to account for any activities that might affect their blood pressure. Prior to test phase, the monitor was initiated (i.e. recoded for a new participant, previous data saved and removed from the monitor). Both monitor and cuff were applied to participants in the morning and collected the following day after 24 hours of testing. Data was then captured and collected using SpaceLabs software that enables the import of data from the sensor. SpaceLabs software automatically calculates the total mean, waking mean and sleeping mean blood pressures; creating graphs of data ready for interpretation.

Statistics

All calculations were performed with the use of Graph Pad prism 5 and Excel. Unpaired student T tests were used to test for homogeneity between groups (P>0.05) and for significant differences between groups (P<0.05). Paired student T testing was also used to determine significance within groups (p<0.05) over the course of the study.

Results

A three month daily intake of red clover extract was shown to attenuate menopause associated losses in BMD (Bone Mineral Density), when compared to placebo.

Vasomotor symptoms, in terms of hot flush frequency were also significantly reduced with treatment, verified by both questionnaires and 24 hour skin conductance. No significant effects associated with treatment were found with respect to lipid profile, inflammation markers and C reactive protein. No significant effects on blood pressure were seen.

Dual X-Ray Absorptiometry

The baseline DXA characteristics of the menopausal women that completed the study are shown in table 4. No statistically significant difference was observed among the different groups. The mean BMD at the femoral neck was >0.795 g/cm$^2$ in both groups that indicating a mean T score value >−1 (a t-score of −1 indicates osteopenia). Most of the women were within the normal range, although standard error of mean (SEM) values suggest that some were either close to or just over threshold (N. Morabito, A. Crisafulli, C. Vergara, A. Gaudio, A. Lasco, N. Frisina, R. D'Anna, F. Corrado, M. A. Pizzoleo, M. Cincotta, D. Altavilla, R. lentile, and F. Squadrito, "Effects of genistein and hormone-replacement therapy on bone loss in early postmenopausal women: a randomized double-blind placebo-controlled study.," *Journal of bone and mineral research: the official journal of the American Society for Bone and Mineral Research*, vol. 17, no. 10, pp. 1904-12, October 2002).

TABLE 4

The baseline (week 0) DXA characteristics of all 60 participants divided into treatment and placebo groups, showing means (above) and SEM (below). Unpaired student T testing (P <0.05) between the groups verified that there were no significant differences.

|  | Treatment (n = 32) | Placebo (n = 28) | Unpaired T Test (P <0.05) |
|---|---|---|---|
| Lumbar spine BMD (g/cm$^2$) | 1.054 | 1.048 |  |
| (SEM) | (0.042) | (0.025) | NS (P = 0.7174) |
| Femoral neck BMD (g/cm$^2$) | 0.913 | 0.850 |  |
| (SEM) | (0.023) | (0.021) | NS (P = 0.0552) |
| Lumbar spine BMC (g) | 50.187 | 48.60 |  |
| (SEM) | (2.171) | (1.600) | NS (P = 0.5595) |
| Femoral neck BMC (g) | 4.310 | 4.081 |  |
| (SEM) | (0.131) | (0.099) | NS (P = 0.1772) |

NS = none significant.

Statistical analysis of in group changes in BMD (table 5) and BMC (table 6), from baseline to week 12, are shown below. Significant reduction between start and end femoral neck BMD occurred in both groups. Within the treatment group the small significant reduction in femoral neck BMD amounted to −1.00%, the femoral neck BMC exhibited a concurrent significant reduction of −1.12%. However, there were no concurrent significant changes to lumbar spine BMD or BMC.

In the placebo group, small significant decrease can be seen in both the femoral neck BMD (−1.27%) and an even larger significant decrease of BMD in the lumbar spine (−1.53%). These two reductions in BMD were greater than in the treatment group.

TABLE 5

The initial and endpoint intragroup BMD characteristics of both treatment and placebo groups, displayed as means and SEM. Paired student T tests of the baseline and endpoint of each variable (lumbar spine, femoral neck) are displayed to the right of the absolute values.

| Variable | Treatment (n = 32) | Paired T Test (P sig. <0.05) | Placebo (n = 28) | Paired T Test (P sig. <0.05) |
|---|---|---|---|---|
| Lumbar spine BMD (g/cm$^2$) (week 0) | 1.054 SEM (0.042) |  | 1.048 SEM (0.025) |  |
| Lumbar spine BMD End (g/cm$^2$) (week 12) | 1.054 SEM (0.042) | NS | 1.035 SEM (0.027) | **0.0026 |
| Femoral neck BMD (g/cm$^2$) (week 0) | 0.913 SEM (0.023) |  | 0.850 SEM (0.021) |  |
| Femoral neck BMD (g/cm$^2$) (week 12) | 0.903 SEM (0.022) | *0.0274 | 0.837 SEM (0.019) | *0.0235 |

*indicates p <0.05 and
**indicates p <0.001,
NS = none significant.

In table 5 it is only the treatment group that expressed a significant decrease in femoral neck BMC (−1.12%), whereas there was no change in BMC in the lumbar spine.

Conversely, the placebo group showed no change in BMC in either location.

TABLE 6

The initial and endpoint intragroup BMC characteristics of both treatment and placebo groups, displayed as means and SEM. Paired student T tests of the baseline and endpoint of each variable (lumbar spine and femoral neck) are displayed to the right of the absolute values.

| Variable | Treatment (n = 32) | Paired T Test (P sig. <0.05) | Placebo (n = 28) | Paired T Test (P sig. <0.05) |
|---|---|---|---|---|
| Lumbar spine BMC (g) (week 0) | 50.187 SEM (2.170) |  | 48.60 SEM (1.600) |  |
| Lumbar spine BMC (g) (week 12) | 50.070 SEM (2.015) | NS | 49.049 SEM (1.825) | NS |
| Femoral neck BMC (g) (week 0) | 4.310 SEM (0.131) |  | 4.081 SEM (0.099) |  |
| Femoral neck BMC (g) (week 12) | 4.262 SEM (0.123) | *0.0324 | 4.049 SEM (0.105) | NS |

*indicates p <0.05
NS = none significant.

The BMDs at the lumber spine and femoral neck regions, taken at the conclusion of the study, are expressed in FIG. 3. There was a significant difference between final femoral neck BMD measurements (graph A) between the placebo and treatment group. Here the treatment group is seen to have a significantly higher BMD compared with the placebo group. Contrary to expectation there was no significant difference in the final BMDs at the lumbar spine between the treatment and placebo groups (graph B). This is most likely owing to the high level of variance apparent in the treatment group. No significant differences were found between any of the initial BMD values of the placebo and treatment groups.

FIG. 4 shows the final (week 12) BMC values at the lumbar spine (B) and femoral neck (A) regions. There was no significant difference in end point femoral neck BMC between the placebo and treatment group. Nor was there any significant difference between the final BMC values in the lumbar spine of placebo and treatment groups. No significant differences were found between any of the initial BMC values of the placebo and treatment groups.

Hot Flush Frequency

FIG. 5 illustrates the changes in HF frequency (means of absolute values and percentage change) from baseline to study conclusion. Both FIGS. 5 and 6 display the final results from the placebo group (n=27) and the treatment group (n=31). One of the data set was removed from each group due to either incompletion (lacking one of the three measurements) or because of poor data quality (fuzzy and not functioning within MatLab). There were no significant differences between start values of placebo and treatment groups. Graph B shows a consistent trend in reduction of HFs over the course of the study. A paired student T test of the data in B revealed a small significant reduction (P 0.0168) in HFs from baseline to the end of the study. In contrast to this, there was no significant intragroup change, from week 0-12, in the placebo group (A).

Graph C, in FIG. 5, depicts the overall percentage change in HFs in both treatment and placebo data sets. From this graph it is apparent that the treatment group has expressed a greater reduction in HFs (−28.14%±SEM 9.60) in comparison to the placebo group that has experienced little change (−2.87%±SEM 10.75).

Hot Flush Intensity

Figure 6:
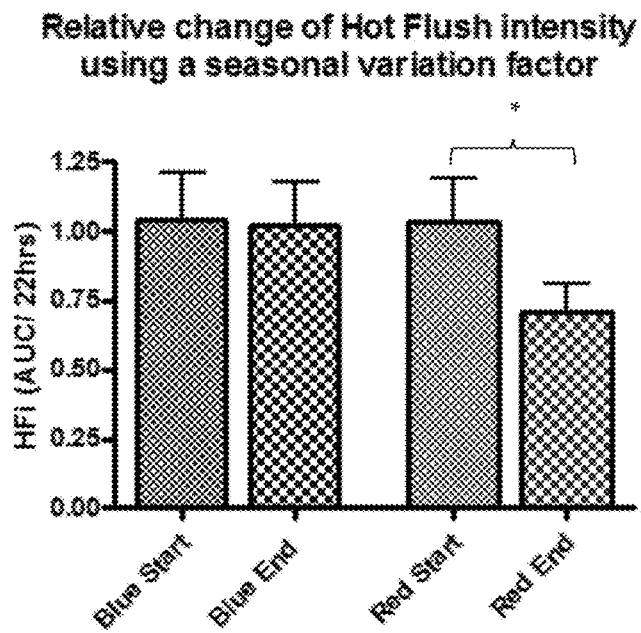

FIG. 6 demonstrates the change in HFi between placebo and treatment groups when accounting for seasonal bias. There was a significant difference found between the baseline and end mean values (P=0.0396) in HFi within the treatment group, HFi was shown to be reduced by 32% when accounting for ambient temperature increases. There was no significant difference between the start and end values of the placebo group.

Questionnaires

Results from the cumulative green menopause index scores for the treatment and placebo groups at the start, the middle and the end of the trial are shown in FIG. 7.

FIG. 7 shows the final green menopause index scores for the vasomotor symptoms section within the index. The graph includes the treatment and placebo groups at the start, middle and end points of the trial. Paired T testing comparing baseline and final values found significant reductions in vasomotor symptom within the treatment group. Paired T tests showed no significant difference between initial and final values of the blue group. Unpaired T test showed that there was no significance between red finish and blue finish results in all three sections.

Inflammation—High Sensitivity C Reactive Protein

Figure 8:
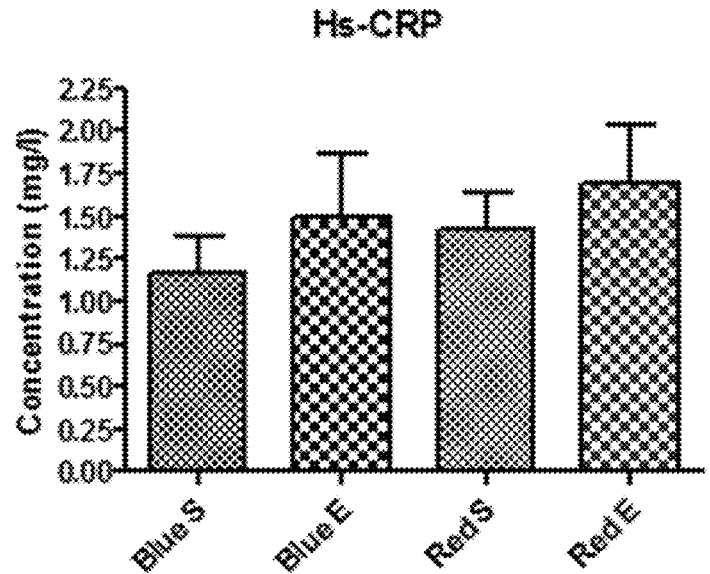

Results from the Hs-CRP assay for placebo (blue) and treatment (red) groups (from baseline to final measurement) are displayed in FIG. 8. Unpaired t testing showed no significant differences between the start values between placebo and treatment groups. Further, paired T testing indicated no significant intragroup differences, between the start and final measurements for Hs-CRP in either group.

Multiplex Bead Array

Because there was a significant difference between some of the start values in the red and blue group, this suggested the presence of potential outliers within the data sets. After further investigation there was identified three participants (in the placebo group) in which their start values were three times greater than their equivalent endpoint measurements, specifically for IL-2, IL-4, IL-5, IL-6, IL-10, IL-12, IL-13 and IFN-γ. Furthermore, these values were found to be significantly larger than red start values. This indicated some degree of abnormal systemic inflammation in these participants at the start of the study. These anomalous results were therefore removed from the data pool in order to ensure that there was no potential bias at the start of measurement between either of the groups.

FIG. 9 shows the results for the baseline and end plasma tests for the mostly pro-inflammatory cytokines IL5, IL 12-p70 and INF-γ. Unpaired t tests revealed no significant differences between the start values between placebo and treatment groups. Further paired T testing indicated no significant intragroup differences, between the start and final measurements, for all the pro-inflammatory factors, IL5 (A), IL 12-p70 (B) and INF-γ (C).

FIG. 10 displays results for the baseline and end plasma tests for the mostly anti-inflammatory cytokines IL10 and IL 13. Unpaired t tests revealed no significant differences between the start values of placebo and treatment groups. Further paired T testing indicated no significant intragroup differences, between the start and final measurements, for all the anti-inflammatory factors, IL-10 (A) and IL-13, in either group.

FIG. 11 displays results for the baseline and end plasma tests for the biphasic (both pro- and anti-inflammatory) cytokines IL-6 (A) and IL-2 (B). Unpaired t tests revealed no significant differences between the start values between placebo and treatment groups. Further paired T testing indicated no significant within group differences, in either group, between the start and final measurements of IL-6 and IL-2.

Lipids

FIG. 12 displays fasted blood plasma total cholesterol (graph A), triglycerides (graph B), LDL (graph C) and HDL (graph D) for the baseline and week 12. Unpaired t tests revealed no significant differences between the start values between placebo and treatment groups in any of the parameters. Further paired T testing indicated no significant changes from baseline to week 12, in either the treatment or placebo group.

Blood Pressure

A table of all 24 hour ambulatory measurements of systolic and diastolic blood pressure is represented below. Table 7 includes the means of absolute values and their corresponding SEMs taken at baseline and week 12. Paired T tests between start and end figures verified non-significance in both treatment and placebo groups. Intragroup differences (not shown), at all points of measurement, were also found to be non-significant when compared by unpaired T testing.

TABLE 7

A graph showing the baseline and final results for the systolic and diastolic blood pressures of treatment and placebo groups. Means (above) and corresponding SEM (below) are shown for each parameter. Paired T tests did not show any significant differences between the start and end values of both treatment and placebo groups.

|  | Treatment (n = 32) | Placebo (n = 28) | Paired T Test (P <0.05) |
|---|---|---|---|
| Systolic (Week 0) | 124.91 | 125.86 |  |
| (SEM) | (1.837) | (2.547) |  |
| Diastolic (Week 0) | 78.63 | 79.82 |  |
| (SEM) | (1.353) | (1.754) |  |
| Systolic (Week 12) | 122.22 | 123.00 |  |
| (SEM) | (2.137) | (2.247) | NS |
| Diastolic (Week 12) | 76.69 | 78.43 |  |
| (SEM) | (1.412) | (1.544) | NS |

Discussion of Results

Red Clover and Bone Health

There was no or little change in the spinal BMD or BMC status within the treatment group (FIGS. 3 A and C, table 5). Firstly, it is thought that the spinal region is more sensitive to estrogen because it contains a higher content of trabecular bone. Secondly, a treatment window of 3 months may only have enabled attenuation to occur in certain locations with faster remodelling rates; for example, spinal remodelling is shown to occur at a higher rate than at the hip. If this is the case, then it can be further postulated that the duration of this study would not proffer adequate treatment time to fully incur a shift from a state of loss attenuation to formation in bone tissues. This may also explain why the significant loss of BMD in femoral tissue of the treatment group was found to be significantly lower than the loss of BMD in the femoral tissue of the placebo group (FIG. 3 B, table 5).

One peculiar finding within this study is that the placebo spinal BMC did not significantly decrease with spinal BMD.

Vasomotor Symptoms and Electrodermal Activity

The results in FIG. 5 demonstrate a significant trend supporting that RC treatment reduces HF frequency to a greater degree than placebo. This improvement is simultaneously lower than some of the previous RC trials and greater than a large proportion of others, all of which use solitary measures for HF frequency (self-reports) [M. Lipovac, P. Chedraui, C. Gruenhut, A. Gocan, C. Kurz, B. Neuber, and M. Imhof, "The effect of red clover isoflavone supplementation over vasomotor and menopausal symptoms in postmenopausal women.," *Gynecological endocrinology: the official journal of the International Society of Gynecological Endocrinology*, vol. 28, no. 3, pp. 203-7, March 2012.; and, P. M. Ridker, C. H. Hennekens, J. E. Buring, and N. Rifai, "C-reactive protein and other markers of inflammation in the prediction of cardiovascular disease in women.," *The New England journal of medicine*, vol. 342, no. 12, pp. 836-43, March 2000]. When contrasting the SC findings with results from the Green Menopause questionnaires, in this trial, the weaknesses of using solitary subjective measurements becomes very apparent. Looking only at the questionnaires, the hypothesis that RC extract can significantly reduce menopause induced vasomotor symptoms would have been debatable, as only the placebo group reported significantly reduced associated menopause symptoms after three months. However, when comparing the subjective (menopause index) to the objective (SC) (together with the vasomotor specific section of the questionnaires) (FIGS. 5 and 7), it is clear that there was a consistent significant reduction in hot flushes within the treatment group. This lies in contrast to no significant change in hot flushes in placebo with SC measures or in the vasomotor section of the questionnaire. This is interesting because it may provide an explanation for the heterogeneity and inconsistency in the results found in previous studies.

Measurements, in this study, were taken between the months March-July of 2012, thus it could be postulated that the incremental improvements seen with HF frequency in the treatment group (FIG. 5 B) were mitigated by ambient temperature with respect to HFi; i.e. the effects of the climate on individual electrodermal conductance responses during middle and especially at the end of the study may have been increasing due to ambient temperature rises. This would explain why the placebo group experienced an increase from baseline HFi at the middle and end points, whereas the treatment groups' baseline sweat secretion remained constant. Laboratory experimentation with SC suggests that a higher electrodermal level (or activity) is induced in males when exposed to hot air when compared with cold [G. Block, C. Jensen, M. Dietrich, E. P. Norkus, M. Hudes, and L. Packer, "Plasma C-reactive protein concentrations in active and passive smokers: influence of antioxidant supplementation.," *Journal of the American College of Nutrition*, vol. 23, no. 2, pp. 141-7, April 2004; and C. Clerici, K. D. R. Setchell, P. M. Battezzati, M. Pirro, V. Giuliano, S. Asciutti, D. Castellani, E. Nardi, G. Sabatino, S. Orlandi, M. Baldoni, O. Morelli, E. Mannarino, and A. Morelli, "Pasta naturally enriched with isoflavone aglycones from soy germ reduces serum lipids and improves markers of cardiovascular risk.," *The Journal of nutrition*, vol. 137, no. 10, pp. 2270-8, October 2007]. This effect becomes apparent when looking at the seasonal factor results (FIG. 6) where there appears to be a trend in reduction in sweat secretion in the treatment group compared to baseline, this is further supported by the normalisation of placebo HFi to levels equivalent to placebo baseline.

Self Report Measures

The results from the questionnaires (FIG. 7) support arguments advocating the use of a parallel objective measure to further supplement self-report measures [E. Mann and M. S. Hunter, "Concordance between self-reported and sternal skin conductance measures of hot flushes in symptomatic perimenopausal and postmenopausal women: a systematic review.," *Menopause (New York, N.Y.)*, vol. 18, no. 6, pp. 709-22, June 2011]. Moreover it provides further evidence supporting that the evaluation of vasomotor symptoms should be executed both independently from and together with other menopause associated symptoms (psychological, sexual dysfunction and physical symptoms) to more accurately assess the efficacy of treatments for menopause [E. Alder, "The Blatt-Kupperman menopausal index: a critique.," *Maturitas*, vol. 29, no. 1, pp. 19-24, May 1998]. The significant improvement to perceived menopause associated symptoms in the placebo group are consistent with the general consensus that menopausal women are a particularly placebo sensitive population group, as seen in other studies. Commonly reported placebo effects are usually in the order of 20-40% [J. A. Eden, "Managing the menopause: phyto-oestrogens or hormone replacement therapy?," *Annals of medicine*, vol. 33, no. 1, pp. 4-6, February 2001; and P. M. Ridker, C. H. Hennekens, J. E. Buring, and N. Rifai, "C-reactive protein and other markers of inflammation in the prediction of cardiovascular disease in women.," *The New England journal of medicine*, vol. 342, no. 12, pp. 836-43, March 2000].

Inflammation—C Reactive Protein

C reactive protein is a key component in the innate immune system is an acute phase protein that is produced by the liver in response to inflammatory cytokines. CRP has been shown to be an effective predictor CVD and biomarker for chronic systemic inflammation [P. M. Ridker, C. H. Hennekens, J. E. Buring, and N. Rifai, "C-reactive protein and other markers of inflammation in the prediction of cardiovascular disease in women.," *The New England journal of medicine*, vol. 342, no. 12, pp. 836-43, March 2000]. The normal physiological concentrations are for CRP are ≤10 mg/l [G. Block, C. Jensen, M. Dietrich, E. P. Norkus, M. Hudes, and L. Packer, "Plasma C-reactive protein concentrations in active and passive smokers: influence of antioxidant supplementation.," *Journal of the American College of Nutrition*, vol. 23, no. 2, pp. 141-7, April 2004]. There was no significant change to CRP levels in either group at baseline or at the end of the study; moreover all CRP concentrations remained within healthy ranges ~1-2.25 mg/l (FIG. 8). This negative finding may be due inter individual variations in metabolite production, for example equol. A recent study by Clerici et al (2007) indicated that 4 weeks of treatment with pasta enriched with 33 mg isoflavone aglycones significantly reduced CRP levels in 62 adults with hypercholesterolemia. These effects were found to be significantly amplified in individuals that were shown to be equol producers [C. Clerici, K. D. R. Setchell, P. M. Battezzati, M. Pirro, V. Giuliano, S. Asciutti, D. Castellani, E. Nardi, G. Sabatino, S. Orlandi, M. Baldoni, O. Morelli, E. Mannarino, and A. Morelli, "Pasta naturally enriched with isoflavone aglycones from soy germ reduces serum lipids and improves markers of cardiovascular risk.," *The Journal of nutrition*, vol. 137, no. 10, pp. 2270-8, October 2007]. It could be postulated that the failure to achieve significance in the current study may be due to limited inclusion of equol producers.

Inflammation—Cytokines and Inflammation Markers

Regrettably this study showed no significant difference in levels of cytokines in the treatment group when compared with placebo (FIGS. 9, 10 and 11). This may be due to the modest dosage given in this trial. There remains heterogeneity in results from previous research concerning human trials, greater success has been achieved with in vitro studies. This suggests that efficacy may be affected by dose concentration distribution between trials, i.e. it is easier to ensure the delivery of a specific dosage to cell lines in contrast to effectively deliver biologically relevant doses to specific locations though-out the human body.

The normal concentration ranges of cytokines in serum samples is specified in the Bio-Plex® suspension array system tech note 6029 "Normal Physiological Levels of Human Cytokines Using Cytokine Assays" that can be found via the following link: http://www.bio-rad.com/webroot/web/pdf/lsr/literature/Bulletin_6029.pdf.

This document recommends use of works by Kokken et al (2010) to determine reference values for normal physiological concentrations of human cytokines in plasma. Using this guideline, the only cytokines that were equivalent to normal ranges were mean INF-γ at 34.10 pg/ml (FIG. 9 graph C) and mean IL-12 at 19.20 pg/ml (FIG. 9 graph B). All the other cytokines detected were within the similar ranges to the patients with onset rheumatoid arthritis, in Kokken et al (2010), specifically IL-2, IL-4, IL-5, IL-6, IL-10 and IL-13 [H. Kokkonen, I. Soderstrom, J. Rocklöv, G. Hallmans, K. Lejon, and S. Rantapää Dahlqvist, "Up-regulation of cytokines and chemokines predates the onset of rheumatoid arthritis.," *Arthritis and rheumatism*, vol. 62, no. 2, pp. 383-91, February 2010]. This finding is consistent with previous research that suggests that postmenopausal women have elevated levels of certain cytokines compared to normal (for example IL-2, IL4, IL 10 and IL-6), it is postulated that this is because of estrogen deficiency [G. Camilleri, M. Borg, S. Brincat, P. Schembri-Wismayer, M. Brincat, and J. Calleja-Agius, "The role of cytokines in cardiovascular disease in menopause.," *Climacteric: the journal of the International Menopause Society*, September 2012; and S. Akyol, S. A. Cinar, S. Purisa, and K. Aydinli, "Relationship between lymphocytes, IL2 and the hormones E2, LH, PRG and FSH in menopausal and postmenopausal women.," *American journal of reproductive immunology (New York, N.Y.: 1989)*, vol. 66, no. 4, pp. 304-9, October 2011; and P. Vural, M. Canbaz, and C. Akgul, "Effects of menopause and postmenopausal tibolone treatment on plasma TNFalpha, IL-4, IL-10, IL-12 cytokine pattern and some bone turnover markers.," *Pharmacological research: the official journal of the Italian Pharmacological Society*, vol. 53, no. 4, pp. 367-71, April 2006]. A remarkable result identified in this study was an elevated level in the cytokines IL 13 and IL 5, there is limited literature specifying the behaviour of IL 13 and IL 5 at menopause. In contrast to this, Yasui et al (2009) showed no deviation from normal physiological serum levels of IL 13 and IL 5 (detected by multiplex) in 66 postmenopausal women [T. Yasui, M. Yamada, H. Uemura, S.-I. Ueno, S. Numata, T. Ohmori, N. Tsuchiya, M. Noguchi, M. Yuzurihara, Y. Kase, and M. Irahara, "Changes in circulating cytokine levels in midlife women with psychological symptoms with selective serotonin reuptake inhibitor and Japanese traditional medicine.," *Maturitas*, vol. 62, no. 2, pp. 146-52, February 2009].

Unfortunately, to knowledge of the author, there appears to be limited research specifically defining the normal physiological levels of cytokines using multiplex technology. Moreover the elevated levels in this trial seem not to be a consequence of anomalous data. There can be seen a good consistency in concentration levels between the participants for all parameters measured, which becomes apparent when looking at the slightness of the T bars representing SEM [FIGS. 7, 8 and 9].

Lipid Status

Normal levels of circulating total fasting blood cholesterol are defined by the 1987 report of the American National Cholesterol Education Program as: <5.19 mmol/l (normal), 5.2-6.19 mmol/l (borderline high risk) and >6.2 mmol/l (High Risk) ["Report of the National Cholesterol Education Program Expert Panel on Detection, Evaluation, and Treatment of High Blood Cholesterol in Adults. The Expert Panel.," *Archives of internal medicine*, vol. 148, no. 1, pp. 36-69, January 1988]. The results [FIG. 10, graph A] suggest that both the placebo and treatment groups are either just within or a little above the normal range for total cholesterol. Typical fasted levels of plasma HDL are 1.2-2 mmol/l in women [FIG. 12, graph D], whereas normal concentrations of LDL are approximately 1.8-3.3 mmol/l [FIG. 12, graph C] and concentrations between 3.3 and 4.1 mmol/l are considered borderline high (associated with higher rates of CVD risk) [[P. Barter, A. M. Gotto, J. C. LaRosa, J. Maroni, M. Szarek, S. M. Grundy, J. J. P. Kastelein, V. Bittner, and J.-C. Fruchart, "HDL cholesterol, very low levels of LDL cholesterol, and cardiovascular events.," *The New England journal of medicine*, vol. 357, no. 13, pp. 1301-10, September 2007]. All of the fasted HDL and LDL concentrations of the participants were within (HDL) or a little below (LDL) the normal range. Both LDL and HDL plasma levels remained constant, with no significant change between the start and end results in either the placebo or the treatment group. Fasting triglyceride plasma concentrations are usually 1.7-2 mmol/l, these leves also remained unchanged in the treatment group when compared with placebo [FIG. 12, graph B] [S. Bansal, J. E. Buring, N. Rifai, S. Mora, F. M. Sacks, and P. M. Ridker, "Fasting compared with nonfasting triglycerides and risk of cardiovascular events in women.," *JAMA: the journal of the American Medical Association*, vol. 298, no. 3, pp. 309-16, July 2007]. Previous research suggests that obese women are more responsive to phytoestrogen treatment; it could be that the effects would be achieved in menopausal women who have dyslipidaemia or are obese. Furthermore, in contrast to other studies, it is conceivable that the dosage given and the duration of the study may not have been adequate to significantly impact lipid profile.

Blood Pressure

In this study there were no significant changes in blood pressure (either systolic or diastolic) between week 0 and week 12 measurements. This is perhaps because the majority of participants were healthy women and therefore changes in BP may be difficult to achieve. Moreover, results show that RC treatment had a null effect on blood pressure equivalent to placebo. This can be considered a beneficial feature of treatment as it suggests that RC treatment can be used in conjunction with other hypotensive or hypertensive medication without effect. A cross over study by Hidalgo et al (2005) of 60 healthy postmenopausal women receiving 80 mg RC isoflavone per day for 90 days also failed to show a significant effect of treatment on blood pressure. They concluded there was growing evidence for various beneficial effects of isoflavones against CVD, i.e. inhibition of platelet aggregation, antioxidant activity, lipid profile modification and effects over the vascular endothelium. However, the previous literature referred to in Hidalgo et al (2005) which provided evidence supporting significant changes to blood pressure included diabetic postmenopausal women [L. A. Hidalgo, P. A. Chedraui, N. Morocho, S. Ross, and G. San Miguel, "The effect of red clover isoflavones on menopausal symptoms, lipids and vaginal cytology in menopausal women: a randomized, double-blind, placebo-controlled study.," *Gynecological endocrinology: the official journal of the International Society of Gynecological Endocrinology*, vol. 21, no. 5, pp. 257-64, November 2005], [J. B. Howes, D. Tran, D. Brillante, and L. G. Howes, "Effects of dietary supplementation with isoflavones from red clover on ambulatory blood pressure and endothelial function in postmenopausal type 2 diabetes.," *Diabetes, obesity & metabolism*, vol. 5, no. 5, pp. 325-32, September 2003]. In this regard, it has been recommended that it might be more useful to measure changes in arterial stiffness as opposed to blood pressure in participants with an already healthy cardiovascular profile [H. J. Teede, B. P. McGrath, L. DeSilva, M. Cehun, A. Fassoulakis, and P. J. Nestel, "Isoflavones reduce arterial stiffness: a placebo-controlled study in men and postmenopausal women.," *Arteriosclerosis, thrombosis, and vascular biology*, vol. 23, no. 6, pp. 1066-71, June 2003].

Conclusion

This study provided evidence that daily ingestion of 37.1 mg (with 33.78 mg as aglycones) preparation of red clover extract over a three month period can attenuate menopause associated losses in BMD, when compared to a placebo. These changes were apparent in both the lumbar spine and femoral neck regions. Unfortunately, there was no reciprocal effect achieved with respect to the participants' BMC (in either location) and no difference from placebo.

In this trial vasomotor symptoms, such as HF frequency, are shown to be significantly reduced by treatment (when examined as separate factor) in the subjective self-report measure and when recorded with objective 24 hour skin conductor. No effect of treatment on HFi was found, although after accounting for ambient temperature a non-significant trend towards reduction in HFi becomes apparent and warrants further research.

Findings from the trial agree with previous research on menopause subject types, in that they were particularly sensitive to the placebo effect. Menopause associated symptoms were found to be significantly reduced in the placebo group when compared with control.

RC treatment did not have any significant effect on the inflammatory cytokines (IL-2, IL-4, IL-5, IL-6, IL-10, IL-12, IL-13 and IFN-γ) or on C-reactive protein levels. An unanticipated outcome from the multiplex assay on the blood test showed that all the women (both placebo and treatment groups) had elevated plasma IL-2, IL-4, IL-5, IL-6, IL-10 and IL-13 when contrasted with normal physiological levels. These were within the same range as individuals with onset rheumatoid arthritis.

Three months of treatment with Red Clover extract had no demonstrable effect on lipid profile (i.e. total cholesterol, triglycerides, HDL or LDL) of healthy fasted menopausal women when compared to placebo.

24 hr ambulatory blood pressure of healthy menopausal women, in this study, failed to demonstrate any significant intra or inter group change (in either treatment or placebo groups) throughout the trial. This may implicate that the use of more sensitive measures (such as arterial resistance) to better elucidate the presence of potential effects.

To summarise this novel Red Clover extract has demonstrable beneficial effects on vasomotor symptoms and bone status on women in the menopause. The Q sensor (Affectiva™) presents a viable option for ambulatory 24 hr measurement of vasomotor symptoms and correlated well with the green menopause index vasomotor score category. No effects were seen in inflammatory factors measured but the elevated levels found in the participants may explain the propensity for increased CVD risk for women during this part of their life.

Conclusion

Red Clover derived isoflavones can attenuate menopause associated BMD (Bone Mineral Density) losses and can reduce vasomotor symptoms when compared to placebo. Skin conductance was an effective method from measuring vasomotor symptoms in affected women and offers a superior alternative and/or strong supplemental measure to subjective self-reports. No effects of Red Clover treatment were found in the lipid profile, inflammatory markers, C reactive protein or blood pressure of the participants. Treatment-induced alterations to these parameters may be difficult to elucidate in healthy menopausal women. Basal levels of IL-2, IL-4, IL-5, IL-6, IL-10 and IL-13 were found to be within the same range as patients with onset rheumatoid arthritis. Self-report measures showed menopausal women to be sensitive to the placebo effect, concurring with previous literature.

Example 3

Goal

The primary scientific goals of the first phase of the project are as follows; 1) to assess the bioavailability of a liquid RC preparation in women in the menopause 2) to determine the efficacy of the RC preparation on menopause symptoms and as a possible attenuator of bone mineral resorption 3) to elucidate the effects of RC on the lipid profile and cardiovascular health of menopausal women. The present study will employ a novel technology (skin conductors) for the measurement of menopausal hot flushes enabling objective physiological measurement of vasomotor symptoms over 24 hours.

The primary scientific goals for phase two of the project are as follows; 1) to compare the efficacy of a combined RC, vitamin D, calcium and magnesium treatment to the standard treatment (vitamin D, calcium and magnesium) proscribed to women with estrogen deficient osteopenia 2) to identify other benefits to heath occurring with treatment (i.e. lipid profile, cardiovascular health and reductions in inflammation). There are currently few existing head to head research trials combining RC isoflavones with the standard vitamin D and calcium treatment often proscribed to sufferers of osteopenia and osteoporosis, hence research in this area can be described as novel. Data comparing combined treatment (isoflavones, vitamin D, calcium and magnesium) against the standard treatment (vitamin D, calcium and magnesium) will assess the extent to which isoflavones can modulate bone re-modelling in conditions of estrogen deficiency and their ability enhance bone mineral distribution and density.

Project Description—Hypothesis

Participants receiving active RC supplementation will have significant reductions in incidence (peak rate) and intensity (total area under the curve) of hot flushes compared with the placebo phase, as determined by 24 hour skin conductance.

Participants receiving active RC supplementation will have normalised (or attenuated) resorption as determined by significant reductions in plasma CTX-I. Significant changes in formation markers and in resorption biomarkers, as well as changes in BMD and BMC will also be determined.

Participants receiving active RC supplementation will have improved fasted lipid profile as determined by LDL and HDL ratio, total cholesterol and triglycerides in both the short and long term, compared with placebo Long and short term administration of both types of red clover formulations (high in isoflavone aglycones) will ensure a high bioavailability during administration and provide measurable quantities representative of biologically relevant doses in urine.

Research Questions

1. Phase 1 of the project will entail the execution of a 6 month (3 months active treatment), double blind, cross-over design, randomised control trial (RCT) using menopausal women. The primary aim is to determine whether daily intake of a fermented RC preparation, in liquid form, can alleviate vasomotor symptoms and associated disorders when compared to a placebo. Research questions addressed by this work package are listed below:
   a. Can RC extract be demonstrated to reduce psychological incidence and intensity of vasomotor symptoms compared to placebo?
   b. Does a daily intake RC extract reduce bone mineral resorption and help stabilise BMD in the short term?
   c. How effective is the RC product at improving cardiovascular health, inducing more positive lipid profile and reducing inflammatory markers?
   d. What influence does the processing method and liquid form of the product have on the bioavailability of isoflavones in the plasma and urine?
2. Phase 2 of the study will entail the execution of a double blind, parallel design, RCT over 12 months using women in the PM, expressing early stage osteopenia (T score <−1 and >−2.5). The primary aim is to determine whether combined red clover, vitamin D, calcium and magnesium treatment is significantly more effective than singular treatment with vitamin D, calcium and magnesium. Research questions addressed by this work package are listed below:
   a. Can a daily treatment of combined RC, Calcium, magnesium and vitamin D attenuate mineral resorption of bone tissue more effectively than the standard treatment (Calcium, magnesium and vitamin D) in the long term?
   b. Does combined RC treatment have positive effects on bone formation and/or bone resorption markers when compared to the standard treatment in the long term?
   c. Are there other detectable beneficial effects to daily RC intake, i.e. promotion of cardiovascular health, improvement of lipid profile and/or reduction of inflammatory markers in the long term?

The Effects of a Novel RC Extract on Menopausal Symptoms and Associated Disorders Research Plan:

We will assess the short term effects of 3 month daily isoflavone treatment on vasomotor symptoms, femoral and lumbar spine BMD, femoral and lumbar spine BMC, fasted plasma lipids and inflammation markers. The aim is to carry out a 6 month, double blind, cross-over design, randomised control trial (RCT). Post-screening participants will be given placebo (phase 1) or treatment (phase 2) for 3 months, washed out and then crossed over to 3 months of the opposing phase. The treatment used in phase 2 will consist of a liquid extract containing ~40 mg/day of isoflavones as aglycones. The primary endpoint of the trial is to demonstrate a significant reduction in vasomotor symptoms (i.e. hot flush frequency and hot flush intensity) within the treatment phase when compared to the placebo phase. An overview of the study design for this work package can be found in the appendices section (FIG. 1).

Perspectives:

Prior research has shown that phytoestrogens exhibit capabilities to improve menopausal vasomotor symptoms, reduce age related bone resorption, reduce inflammation and promote a positive lipid profile in menopausal women. The vast majority of these benefits are thought to be due to their inherent chemical structures enabling isoflavones to bind to estrogen receptors (ERs). Indeed, it is isoflavones are thought to be responsible for the lower rate of reported menopause symptoms in Asia because of their high daily intake of soy (high in genistein and daidzein). The selective ER binding affinity of isoflavones enables these compounds to adopt the regulatory roles of estrogen at target tissue sites during states of estrogen deficiency and/or dysregulation. Their selectivity for ERβ eliminates the breast and endometrial cancer risks that are associated with estrogen treatment. It is therefore of interest to determine whether red clover derived isoflavones can impart beneficial effects due to their ERβ affinity.

Methods and Activities

Participants:

The participants will be menopausal women, aged between 40 and 65, with a follicle stimulating hormone level representative of menopause (≥35 UI/L), that report regular hot flushes. Participants will be recruited through the hospital, by practicing doctors within the local area, hospital clinics and through announcements in local newspapers and flyers. A minimum of 22 Participants are to be included in the trial and will thereafter be randomised into either the placebo or red clover treatment phases. After completion of the initial 3 months, participants will be washed out and then crossed-over to the requisite placebo or red clover phase for the final 3 months of the study.

The Extract:

The RC extract, produced by Herrens Mark ApS, Nr Aaby, is a unique product that will be utilised in this work. The product has been processed by fermentation in order to convert the isoflavone glycoside molecules to a more bioavailable aglycone structure (the product is made by the method described in Example 1). The composition of isoflavones, standardisation and bioavailability of the RC extract will be assessed using High Performance Liquid Chromatography and Mass Spectrometry (HPLC/MS). The product is registered a nutraceutical supplement and natural herbal extract.

Metabolomics:

Fasted urine samples will be taken during the project for analysis using metabolomics at weeks 0 and 12 for both phases. Sample stability will be assessed by solid phase extraction, then separated using HPLC and rp-HPLC, then purified using semi-prep HPLC. Metabolite structures will be elucidated by spectroscopic and spectrometric methods (i.e. 1D and 2D NMR, UV and LC-MS). This will enable evaluation of the uptake and bioavailability of the isoflavone preparation. Tests in this area will assess the processing method's effect on the biological efficacy of the product.

Dual-Energy X-Ray Absorptiometry:

BMD and BMC will be assessed by DEXA at baseline (week 0) and week 12 during both phases, using the XR 800 DEXA scanner (Norland cooper, surgical, USA, illuminatus software version 4.2.4). The tests will be performed under the supervision and guidance of healthcare professional, participants will be scanned for 15-20 minutes. During the scan, measurements of the BMC (g) and BMD (g/cm$^2$) at the lumbar spine region (L2-L4) and at the femoral neck will be taken.

Biomarkers for Inflammation and Lipid Status:

The Bio-rad multiplex Assay for inflammatory markers will be used to analyse blood samples (taken at weeks 0 and 12 in both phases). The following plasma markers will be measured at both the start and end of each 3 month treatment period: IL-2, IL-4, IL-5, IL-6, IL-10, IL-12, IL-13 and IFN-γ. This will help determine the safety profile of the extract.

Analysis of Blood Lipids:

Fasted blood samples will be taken at weeks 0 and 12 for both the initial and cross-over periods of the study and assessed at the endpoint of trial using a Dimension Vista analyser (Dade Behring, Newark, Nebr.) that combines four technologies (i.e. photometry, nephelometry, V-LYTE integrated multisensory potentiometry, and LOCI chemiluminescence). Total cholesterol (TC), high-density lipoprotein cholesterol (HDL-C), low-density lipoprotein (LDL) and triglyceride (TG) concentrations will be measured on using an immunonephelometry assay. This will help determine effects (if any) of the extract on lipid metabolism.

Skin Conductance:

24 hour ambulatory measurements of participant's skin conductance (SC) will be taken at weeks 0, 6 and 12 during both the placebo and treatment phases (pre- and post-crossover). SC will be measured using the Q sensor from Affectiva™ that enables measurements of electrodermal activity outside the laboratory. The Affectiva Q sensor is applied to the wrist (in a similar fashion to a watch) allowing integrated dual electrodes contact with the ventral side of the arm. The electrodes measure the sweat secretion of a participant (in μSiemans), enabling the physiological quantification and qualification of hot flushes over 22 hours (2 hrs of the total 24 hrs used as a buffer during data sampling).

Statistics:

All calculations will be performed with the use of GraphPad prism 6 and Excel. Paired student T tests will be used to test for homogeneity between groups (P>0.05) and for significant differences between placebo and treatment phases (P<0.05). Paired student T testing will be used to determine significance within groups (p<0.05) over the course of the study.

Power Calculation:

The primary endpoint of the trial is to demonstrate a significant reduction in vasomotor symptoms (i.e. hot flush frequency and hot flush intensity) of the treatment phase when compared the placebo phase. To determine the required number of participants the following calculation was used: N=(Za+Zb) 2×s2/MIREDIF2, where N is the number of participants to be included in an unpaired test. Minimum relevant difference was set at 4%; significance level, (a) was set at 5% and b was set to 20%, the spread, s, was set to 6.2. Over and above the final subject inclusion value there was also taken into account those individuals that may withdraw from the trial post-project start (dropouts or withdrawals). The final total number to include is approx. 22 participants; this total is set to ~0-20% over and above the original required number to include value.

The Effects of Long Term Novel Red Clover Treatment on Bone Tissue Regulation in Women with Early Onset Osteopenia Research Plan:

The aim in this study is to carry out a double blind, parallel, 12 month RCT using PM women, with osteopenia (T score between −1 and −2.5) and a tendency for further development of osteoporosis (CTX-I >400 pg/ml). Both placebo and treatment groups will receive daily vitamin D, calcium, magnesium and vitamin mixture supplementation; the treatment group will receive a daily liquid red clover extract high in isoflavones (particularly formononetin) and the placebo group will receive an equivalent placebo liquid.

Secondary aims are to determine whether the bioactive compounds in RC can reduce the biomarkers for cardiovascular disease.

The treatment group will receive a standardised liquid extract containing 48 mg/day of RC derived isoflavones and, along with placebo group, receive the normal prescribed dose of calcium (800-900 mg/d), magnesium (400-450 mg/d) and vitamin D (30-40 μg/d) and a standard vitamin pill for PM women with osteopenia for a period of 12 months. The isoflavones are primarily on the aglycone form. 48 mg of isoflavones primarily on the aglycone form will have the same effect as 78 mg of isoflavones on the glycone form. Plasma biomarkers of isoflavone intake and estradiol will be used as compliance detected using LC-PDA-MS/MS. This will allow for the identification of possible preventive or anabolic effects of isoflavones in osteopenia. Depending on the difference between the preliminary results (at month 6 of the study) of the two groups, a decision will be made to extend the length of the trial by 6 or 12 further months on top of the originally planned study period (1 year). The appropriate application to the Ethics Committee of Central Jutland and the acquisition of the participants consent to continue in the project will take place as soon as a decision regarding the extension is finalised.

Perspectives:

Background literature suggests that certain phytoestrogens are able to affect inter-cellular signalling, cellular differentiation and remodelling activity of bone cells. Hence, isoflavones are shown to exhibit some capacity to affect, either directly and/or indirectly, the regulatory processes of bone tissue. It is generally accepted that ~1-2% of BMD from the lumbar spine region and 1-1.5% of BMD from the femoral neck region are lost per year in post-menopausal women due to dysregulation and deficiency of estrogen. It is therefore valuable to determine whether treatment with RC can promote a normal remodelling cycle due to its high content of isoflavones. Moreover, it would be interesting to assess whether the bioactive effect of isoflavones can enhance the performance of vitamin D, calcium and magnesium treatment in women with age-related osteopenia. Hormone replacement therapy is known to be effective at restoring normal bone mineral turnover but is associated with increased cancer risk; in this regard isoflavones have the potential to provide similar beneficial effects without incurring the same risks as treatment with estrogen. It is therefore of scientific and medical value to identify how effective these compounds are at blunting the accelerated bone mineral resorption that coincides with age-related estrogen deficiency.

Methods and Activities

Participants:

The participants in this work package will be PM women aged between 60 and 85 with osteopenia (T score between −1 and −2.5) and a tendency for further development of osteoporosis (CTX-I >400 pg/ml). Participants will be recruited through the hospital, by practising doctors within the local area, hospital clinics and through advertisements in local newspapers and flyers. A minimum of 60 Participants will be included in the trial and will be randomised into both treatment and placebo groups.

The Extract:

The RC extract to be used in the study will be produced by HerrensMark ApS, Nr Aaby (by the method described in Example 1) and used during this study. The product will be designed as a liquid extract containing 48 mg/day of isoflavones. The product is processed by fermentation in order to convert the isoflavone glycoside molecules to a more bioavailable aglycone structure. The composition of isoflavones and standardisation of the RC extract will be assessed using High Performance Liquid Chromatography and Mass Spectrometry (HPLC/MS).

Metabolomics:

Fasted urine samples will be taken during the project (at weeks 0, 26 and 56) for analysis using metabolomics. Sample stability will be assessed by solid phase extraction, then separated using HPLC and rp-HPLC, and then purified using semi-prep HPLC. Metabolite structures will be elucidated by spectroscopic and spectrometric methods (i.e. 1D and 2 D NMR, UV and LC-MS). This will enable evaluation of the uptake and bioavailability of the isoflavone preparation. Tests in this area will assess the processing method's effect on the biological efficacy of the product.

Dual-Energy X-Ray Absorptiometry:

BMD and BMC will be assessed by DEXA at screening (week −2), week 26 and week 56 using the XR 800 DEXA scanner (Norland cooper, surgical, USA, illuminatus software version 4.2.4). The tests will be performed under the supervision and guidance of healthcare professional, participants will be scanned for 15-20 minutes. The tests will measure the BMC (g) and BMD (g/cm$^2$) at the lumbar spine region (L2-L4) and at the femoral neck. These will be carried out by at the hospital by a relevant healthcare professional.

Biomarkers of Bone Turnover:

A quantification of biomarkers at weeks −2, 26 and 52 will be performed using HPLC, immunosorbant assay, radioimmunoassay and electrochemiluminescence techniques. Plasma bone specific alkaline phosphotase (BS-ALP), total alkaline phosphatase (TALP), N-terminal propeptide of type I procollagen (PINP), C-terminal propeptide of type 1 collegen (PICP) and osteocaclin (OC) will be used as indicators of tissue formation and N-terminal telopeptide (NTX-I), CTX-I will serve as markers for resorption. Moreover, urinary pyridinoline (PD) and deoxypyridinoline (DPD) will be utilised as markers for resorption.

Biomarkers for Inflammation and Lipid Status:

The Bio-rad multiplex Assay for inflammatory markers will be used to analyse the following plasma markers at the start (week −2) and end of (week 52) months of treatment: IL-2, IL-4, IL-5, IL-6, IL-10, IL-12, IL-13 and IFN-γ. This will help determine the safety profile of the extract.

Analysis of Blood Lipids:

Fasted blood samples will be taken at weeks 0, 26 and 56 of the study and assessed at the endpoint of trial using Dimension Vista analyser (Dade Behring, Newark, Nebr.) that combines four technologies (i.e. photometry, nephelometry, V-LYTE integrated multisensory potentiometry, and LOCI chemiluminescence). TC, HDL-C and TG concentrations will be measured on using immunonephelometry assay. This will help determine effects (if any) of the extract on lipid metabolism.

Statistics:

All calculations will be performed with the use of GraphPad prism 6 and Excel. Unpaired student T tests were used to test for homogeneity between groups (P>0.05) and for significant differences between placebo and treatment groups (P<0.05). Paired student T testing will be used to determine significance within groups (p<0.05) over the course of the study.

Power Calculation:

The primary endpoint of the trial is the stabilisation bone mineral resorption as determined by the plasma CTX-I of the treatment group when compared to the placebo group. To determine the required number of participants the following calculation was used: N=(Za+Zb) 2×s2/MIREDIF2, where N is the number of participants to be included in an unpaired test. Minimum relevant difference was set at 2%; significance level, (a) was set at 5% and b was set to 20%, the spread, s, was set to 2.5. Over and above the final subject inclusion value there was also taken into account those individuals that may withdraw from the trial post-project start (drop-outs or withdrawals). The final total number to include is approx. 30 participants per group, this total is set to ~10-20% over and above the original required number to include value.

Items

The present invention is in one embodiment characterized by one or more of the items herein below. These items should not be considered as patent claims.

1. A composition comprising a red clover extract and one or more lactic acid bacteria species.

2. A composition comprising isoflavones isolatable from red clover and one or more lactic acid bacteria species.

3. A composition comprising a red clover extract obtainable by contacting the red clover extract with one or more lactic acid bacteria species.

4. A composition comprising red clover aglycone isoflavones and essentially no glycone isoflavones, wherein said composition is obtainable by a method comprising the steps of providing, processing and fermenting red clover with one or more lactic acid bacteria species.

5. A composition comprising a red clover extract obtainable by a method comprising the steps of
i) providing a red clover extract
ii) providing one or more lactic acid bacteria species
iii) fermenting said red clover extract with said one or more lactic acid bacteria species, and
iv) obtaining a fermented red clover extract.

6. A composition comprising aglycone isoflavones isolatable from red clover and essentially no glycosylated isoflavones.

7. A composition comprising aglycone isoflavones isolatable from red clover and essentially no glycosylated isoflavones and essentially no saccharide residues resulting from the cleavage of said saccharide residues from the glycone form of said isoflavones.

8. The composition according to any of the previous items, wherein an aqueous extract of Dandelion is added to the composition.

9. The composition according to any of the previous items, wherein more than at least 90% of the isoflavones are on an aglycone form.

10. The composition according to any of the previous items, wherein the composition comprises at least one isoflavone selected from the group consisting of biochanin A and Formononetine, including a combination of both.

11. A composition according to any of items 1 to 10 for use as a medicament.

12. A composition according to any of items 1 to 10 for use of treatment of menopause-related symptoms, such as one or more of hot flashes, perspiration, and headache.

13. A composition according to any of items 1 to 10 for use of treatment of premenstrual syndrome.

14. A composition according to any of items 1 to 10 for use of treatment of osteoporosis.

15. A composition according to any of items 1 to 10 for use of treatment of arteriosclerosis.

16. A composition according to any of items 1 to 10 for use of treatment of cholesterol plaques.

17. A composition according to any of items 1 to 10 for use of treatment of hypertension.

18. A composition according to any of items 1 to 10 for use of treatment of cardiovascular diseases.

19. A composition according to any of items 1 to 10 for use of treatment of one or more cancer diseases such as treatment of B-cell precursor (BCP)-leukemia, breast cancer and colorectal cancer.

20. A method of treatment of an individual suffering from, or at risk of developing, menopause-related symptoms, such as one or more of hot flashes, perspiration, and headache, said method comprising the steps of administering to said individual the composition according to any of items 1 to 10, wherein said treatment is prophylactic, ameliorating or curative.

21. A method of treatment of an individual suffering from, or at risk of developing, premenstrual syndrome, said method comprising the steps of administering to said individual the composition according to any of items 1 to 10, wherein said treatment is prophylactic, ameliorating or curative.

22. A method of treatment of an individual suffering from, or at risk of developing, osteoporosis, said method comprising the steps of administering to said individual the composition according to any of items 1 to 10, wherein said treatment is prophylactic, ameliorating or curative.

23. A method of treatment of an individual suffering from, or at risk of developing, arteriosclerosis, said method comprising the steps of administering to said individual the composition according to any of items 1 to 10, wherein said treatment is prophylactic, ameliorating or curative.

24. A method of treatment of an individual suffering from, or at risk of developing, cholesterol plaques, said method comprising the steps of administering to said individual the composition according to any of items 1 to 10, wherein said treatment is prophylactic, ameliorating or curative.

25. A method of treatment of an individual suffering from, or at risk of developing, hypertension, said method comprising the steps of administering to said individual the composition according to any of items 1 to 10, wherein said treatment is prophylactic, ameliorating or curative.

26. A method of treatment of an individual suffering from, or at risk of developing, cardiovascular diseases, said method comprising the steps of administering to said individual the composition according to any of items 1 to 10, wherein said treatment is prophylactic, ameliorating or curative.

27. A method of treatment of an individual suffering from, or at risk of developing, a cancer disease, such as B-cell precursor (BCP)-leukemia, breast cancer and colorectal cancer, said method comprising the steps of administering to said individual the composition according to any of items 1 to 10, wherein said treatment is prophylactic, ameliorating or curative.

28. A method of making a fermented red clover extract comprising the steps of
i) providing a red clover extract
ii) providing one or more lactic acid bacteria species
iii) fermenting said red clover extract with said one or more lactic acid bacteria species, and
iv) obtaining a fermented red clover extract.

The invention claimed is:
1. A method of making a composition comprising aglycone red clover isoflavones, the method comprising:
heating red clover to a temperature in the range of 40° C. to 100° C. for at least 15 minutes;
compressing the heated red clover to produce a liquid red clover extract;
fermenting the liquid red clover extract with one or more lactic acid bacteria species at a temperature in the range of 0° C. to 30° C. for at least 2 weeks; and
obtaining the composition from the fermented red clover extract.

2. The method according to claim 1, wherein at least 90% of the red clover isoflavones are in an aglycone form in the composition.

3. The method according to claim 1, wherein the fermenting is performed at a temperature in the range of 3° C. to 10° C.

4. The method according to claim 1, wherein the fermenting is performed at a first fermentation temperature in the range of 22° C. to 25° C. for up to 3 days and then at a second temperature in the range of 15° C. to 17° C. for at least 2 weeks.

5. The method according to claim 4, further comprising lowering the second temperature to a third fermentation temperature in the range of 3° C. to 5° C.

6. The method according to claim 1, wherein the fermenting is performed at a first fermentation temperature in the range of 20° C. to 24° C. for up to 5 days and then at a second temperature in the range of 15° C. to 20° C. for at least 2 weeks.

7. The method according to claim 6, further comprising lowering the second fermentation temperature to a third fermentation temperature in the range of 3° C. to 5° C.

8. The method according to claim 1, wherein the red clover is fresh red clover.

9. The method according to claim 8, wherein the liquid red clover extract prior to fermenting has a total dry matter content of about 6.6% (m/m).

10. The method according to claim 1, wherein a fermented dandelion extract is added to the liquid red clover extract.

11. The method according to claim 1, wherein the fermented red clover extract has a dry matter content in the range of 3% (m/m) to 5% (m/m).

12. The method according to claim 1, further comprising transferring the red clover extract obtained after fermenting to a new container at an interval in the range of 1 to 12 weeks.

13. The method according to claim 1, wherein the fermented red clover extract has a pH in the range of about 1 to about 5.

14. The method according to claim 1, wherein the red clover is *Trifolium pratense, T. pratense americanum, T. pratense* frigidum, *T. pratense maritimum, T. pratense parviflorum, T. pratense sativum, T. pratense villosum,* or the *T. pratense* L varieties *Rajah*, Nordi, Jesper, Joioinen, or Pawera.

15. The method according to claim 1, wherein the one or more lactic acid bacteria is *Lactobacillus* spp. and *Bifidobacterium* spp, or a combination of *Lactobacillus* spp. and *Bifidobacterium* spp.

16. The method according to claim 1, further comprising formulating the composition as a pill, capsule, gel, mixture, liquid composition, liquid mixture, or a powder.

17. The method according to claim 1, further comprising adding one or more of a sweetener, a carbohydrate source, a fat source, a flavouring agent, a vitamin, a mineral, an electrolyte, or a trace element to the composition.

18. The method according to claim 1, further comprising adding a dandelion extract to the liquid red clover extract.

19. The method according to claim 1, wherein the temperature in the heating step is in the range of 60° C. to 100° C.

20. The method according to claim 2, wherein the isoflavone in an aglycone form is selected from the group consisting of biochanin A and Formononetin, and combinations thereof.

21. The method according to claim 1, wherein the composition comprises Formononetin and Ononin, and the content of Formononetin is at least 90% of the sum of Formononetin and Ononin.

22. A method of making a composition comprising Formononetin and Ononin, the method comprising:
   compressing red clover to produce a liquid red clover extract;
   fermenting the liquid red clover extract with one or more lactic acid bacteria species at a temperature in the range of 0° C. to 20° C. for at least 2 weeks; and
   obtaining the composition from the fermented red clover extract, which composition comprises at least 90% Formononetin compared to the sum of Formononetin and Ononin.

23. The method according to claim 22, wherein no lactic acid bacteria are added to the red clover extract.

24. A method of making a composition comprising Formononetin and Ononin, the method comprising:
   heating red clover to a temperature in the range of 40° C. to 100° C. for at least 15 minutes;
   compressing the heated red clover to produce a liquid red clover extract;
   fermenting the liquid red clover extract with one or more lactic acid bacteria species at a temperature in the range of 0° C. to 40° C. for at least 2 weeks; and
   obtaining the composition from the fermented red clover extract, which composition comprises at least 90% Formononetin compared to the sum of Formononetin and Ononin.

25. The method according to claim 24, wherein the temperature in heating step is the range of 60° C. to 100° C.

* * * * *